United States Patent
Sewell et al.

(10) Patent No.: US 12,053,513 B2
(45) Date of Patent: Aug. 6, 2024

(54) CANCER-SPECIFIC T-CELL RECEPTORS

(71) Applicant: UNIVERSITY COLLEGE CARDIFF CONSULTANTS LTD., Cardiff South Wales (GB)

(72) Inventors: Andrew Sewell, Cardiff South Glamorgan (GB); Garry Dolton, Cardiff South Glamorgan (GB)

(73) Assignee: University College Cardiff Consultants Ltd., Cardiff South Wales (GB)

( * ) Notice: Subject to any disclaimer, the term of this patent is extended or adjusted under 35 U.S.C. 154(b) by 613 days.

(21) Appl. No.: 17/119,899

(22) Filed: Dec. 11, 2020

(65) Prior Publication Data

US 2021/0196807 A1   Jul. 1, 2021

Related U.S. Application Data

(63) Continuation of application No. PCT/GB2019/051785, filed on Jun. 25, 2019.

(30) Foreign Application Priority Data

Jun. 25, 2018 (GB) .................................. 1810358

(51) Int. Cl.
| | |
|---|---|
| *A61K 38/00* | (2006.01) |
| *A61K 38/08* | (2019.01) |
| *A61K 39/00* | (2006.01) |
| *A61P 35/00* | (2006.01) |
| *C07K 7/06* | (2006.01) |

(52) U.S. Cl.
CPC .......... *A61K 39/0011* (2013.01); *A61K 38/08* (2013.01); *A61P 35/00* (2018.01); *C07K 7/06* (2013.01); *A61K 2039/70* (2013.01)

(58) Field of Classification Search
CPC ..... A61K 39/0011; A61K 38/08; A61P 35/00; C07K 7/06; C07K 14/4748
See application file for complete search history.

(56) References Cited

U.S. PATENT DOCUMENTS 9,808,504 B2 * 11/2017 Dhodapkar .... A61K 39/001152

FOREIGN PATENT DOCUMENTS

WO   WO-2016187508 A2   11/2016

OTHER PUBLICATIONS

Galloway et al Frontiers in Immunology vol. 10, Article 319, 18 pages (Mar. 2019), (Year: 2019).*
Skwarczynski et al, Chem. Sci. vol. 7 p. 842 (2016) (Year: 2016).*
Sercarz et al, Annual Review of Immunology vol. 11 p. 729 (1993) (Year: 1993).*
Theaker "Developing Peptide Vaccines for Breast Cancer" May 2018, 228 pages. (Year: 2018).*
Knutson, Keith L., et al. "Immunization of Cancer Patients with a HER-2/neu, HLA-A2 Peptide, p. 369-377, Results in Short-lived Peptide-specific Immunity." *Clinical Cancer Research* 8.5 (2002): 1014-1018.
Gagnon, Susan J., et al. "Extensive T cell receptor cross-reactivity on structurally diverse haptenated peptides presented by HLA-A2." *Molecular Immunology* 43.4 (2006): 346-356.
Zhao, Yingdong, et al. "Combinatorial Peptide Libraries and Biometric Score Matrices Permit the Quantitative Analysis of Specific and Degenerate Interactions Between Clonotypic TCR and MHC Peptide Ligands." *The Journal of Immunology* 167.4 (2001): 2130-2141.
Andersen, Rikke, et al. "Long-Lasting Complete Responses in Patients with Metastatic Melanoma after Adoptive Cell Therapy with Tumor-Infiltrating Lymphocytes and an Attenuated IL2 Regimen." *Clinical Cancer Research* 22.15 (2016): 3734-3745.
Ekeruche-Makinde, Julia, et al. "T-cell Receptor-optimized Peptide Skewing of the T-cell Repertoire can Enhance Antigen Targeting." *Journal of Biological Chemistry* 287.44 (2012): 37269-37281.
Haney, Danielle, et al. "Isolation of viable antigen-specific CD8+ T cells based on membrane-bound tumor necrosis factor (TNF)-α expression." *Journal of Immunological Methods* 369.1-2 (2011): 33-41.
Donia, Marco, et al. "PD-1+ Polyfunctional T Cells Dominate the Periphery after Tumor-Infiltrating Lymphocyte Therapy for Cancer." *Clinical Cancer Research* 23.19 (2017): 5779-5788.
Szomolay, Barbara, et al. "Identification of human viral protein-derived ligands recognized by individual MHCI-restricted T-cell receptors." *Immunology and Cell Biology* 94.6 (2016): 573-582.
Ekeruche-Makinde, Julia, et al. "Peptide length determines the outcome of TCR/peptide-MHCI engagement." *Blood* 121.7 (2013): 1112-1123.
Tungatt, Katie, et al. "Antibody Stabilization of Peptide-MHC Multimers Reveals Functional T Cells Bearing Extremely Low-Affinity TCRs." *The Journal of Immunology* 194.1 (2015): 463-474.
Legut, Mateusz, et al. "CRISPR-mediated TCR replacement generates superior anticancer transgenic T cells." *Blood* 131.3 (2018): 311-322.

(Continued)

*Primary Examiner* — Sheela J. Huff
(74) *Attorney, Agent, or Firm* — Dechert LLP; Andrew T. Wilkins

(57) ABSTRACT

The present disclosure relates to a new anti-cancer peptide; a vector encoding same; a pharmaceutical composition or immunogenic agent or bispecific or vaccine comprising said anti-cancer peptide; use of said anti-cancer peptide, vector, pharmaceutical composition, immunogenic agent, bispecific or vaccine to treat cancer; a method of treating cancer using said anti-cancer peptide, vector, pharmaceutical composition, immunogenic agent, bispecific or vaccine; and a combination therapeutic for the treatment of cancer comprising said anti-cancer peptide, vector, pharmaceutical composition, immunogenic agent, bispecific or vaccine.

Figure 1A:
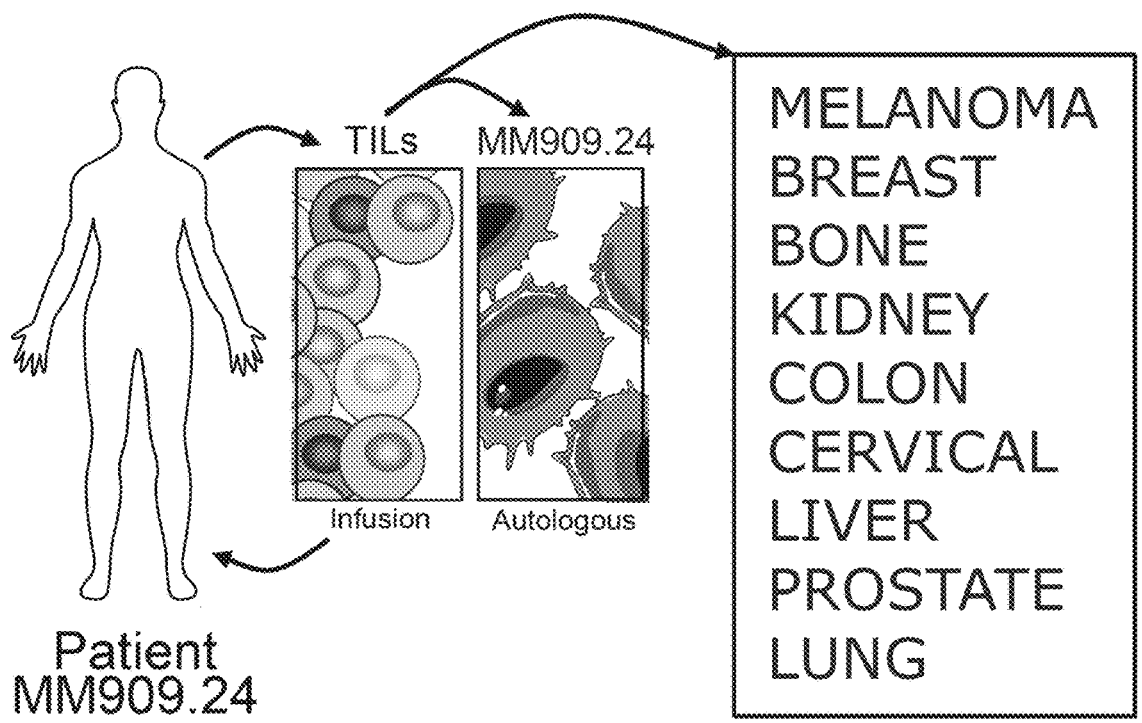

19 Claims, 24 Drawing Sheets
Specification includes a Sequence Listing.

(56) References Cited

OTHER PUBLICATIONS

Hundemer, Michael, et al. "Identification of a new HLA-A2-restricted T-cell epitope within HM1.24 as immunotherapy target for multiple myeloma." *Experimental Hematology* 34.4 (2006): 486-496.
Bianchi, Valentina. "Molecular and Cellular Basis of T-cell Responses to Melanoma Antigens." *Diss. Cardiff University*, 2016.
Wooldridge L., et al. "A Single Autoimmune T Cell Receptor Recognizes More Than a Million Different Peptides." *J Biol. Chem.* 2012;287:1168-77.
International Search Report and Written Opinion for International Application No. PCT/GB2019/051785, dated Sep. 23, 2019, 11 pages.
Matsushita, S., "[Novel strategies for peptide-based immunotherapy: identification of peptide superagonists using combinatorial peptide libraries and mass spectrometry]," Arerugi[Allergy] 1999 48(11): 1200-1205.

\* cited by examiner

The pie chart shows the proportion of TCRs (segments) able to recognise multiple cancer cell lines (numbers).

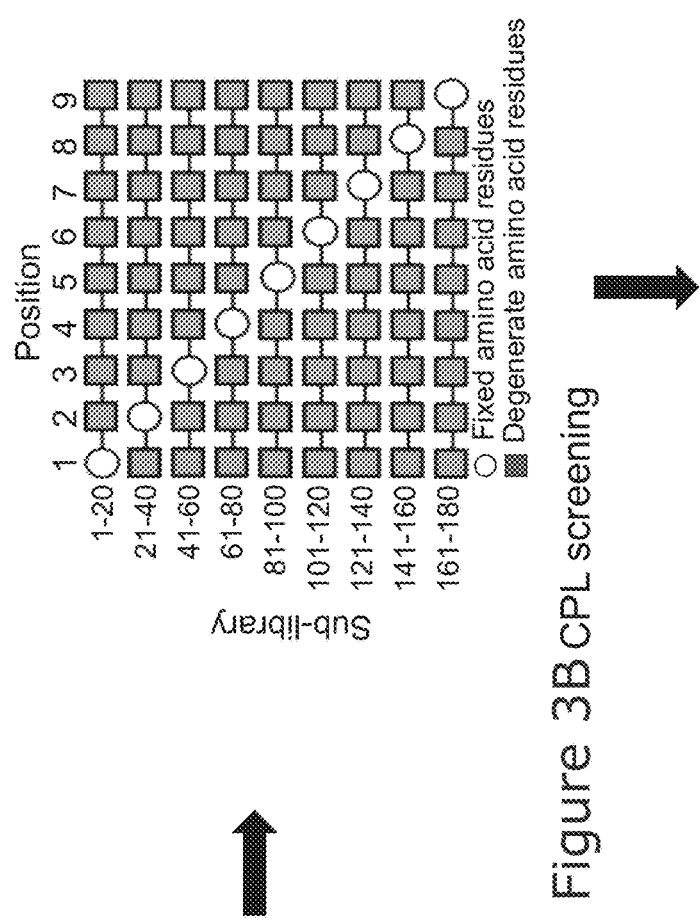
Figure 3B CPL screening
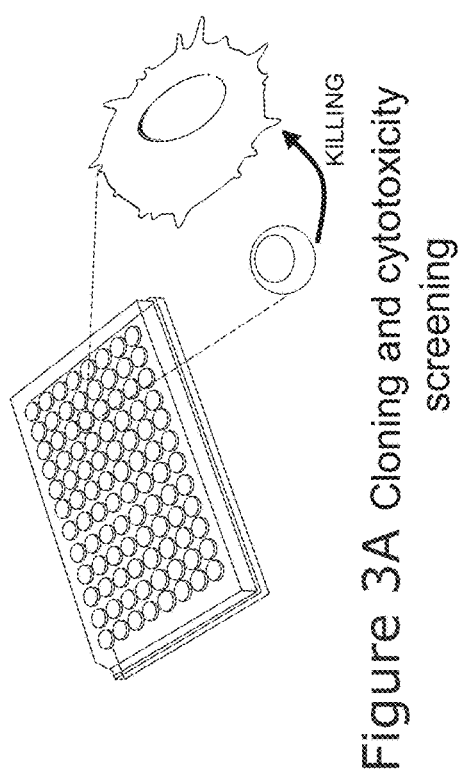
Figure 3A Cloning and cytotoxicity screening
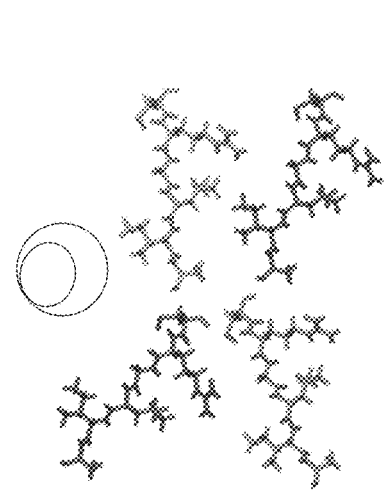
Figure 3C Cancer antigen database
Figure 3D Testing candidate peptides

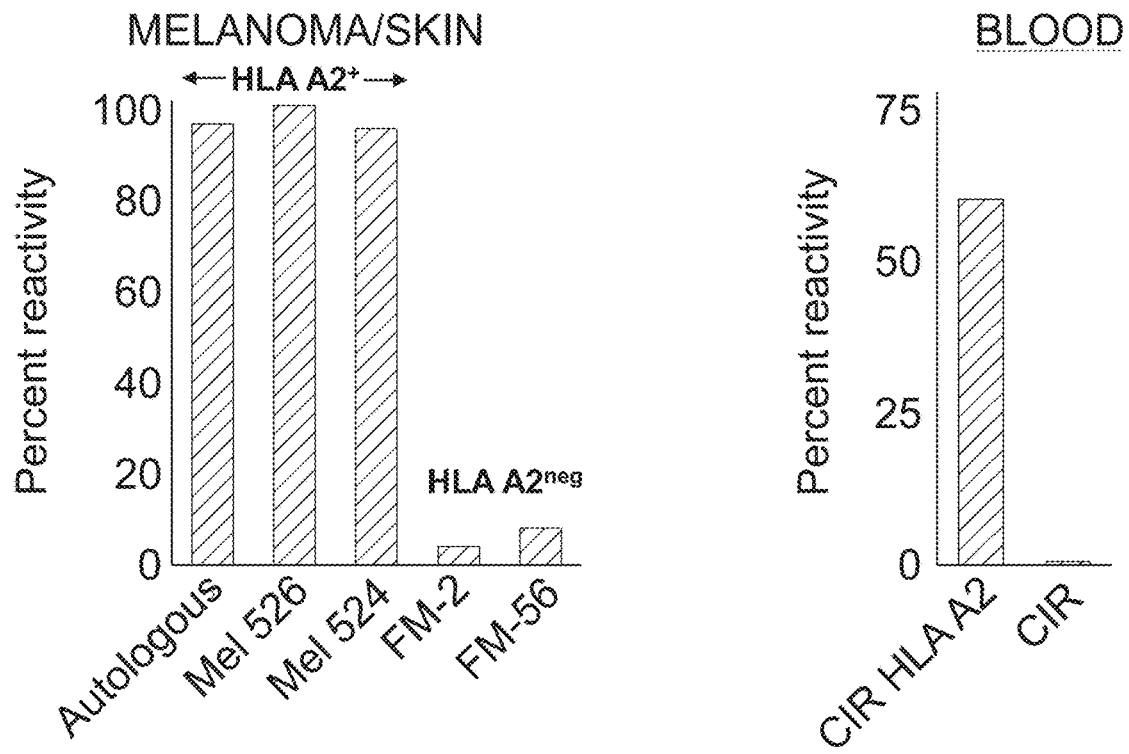
Figure 4A
Figure 4B
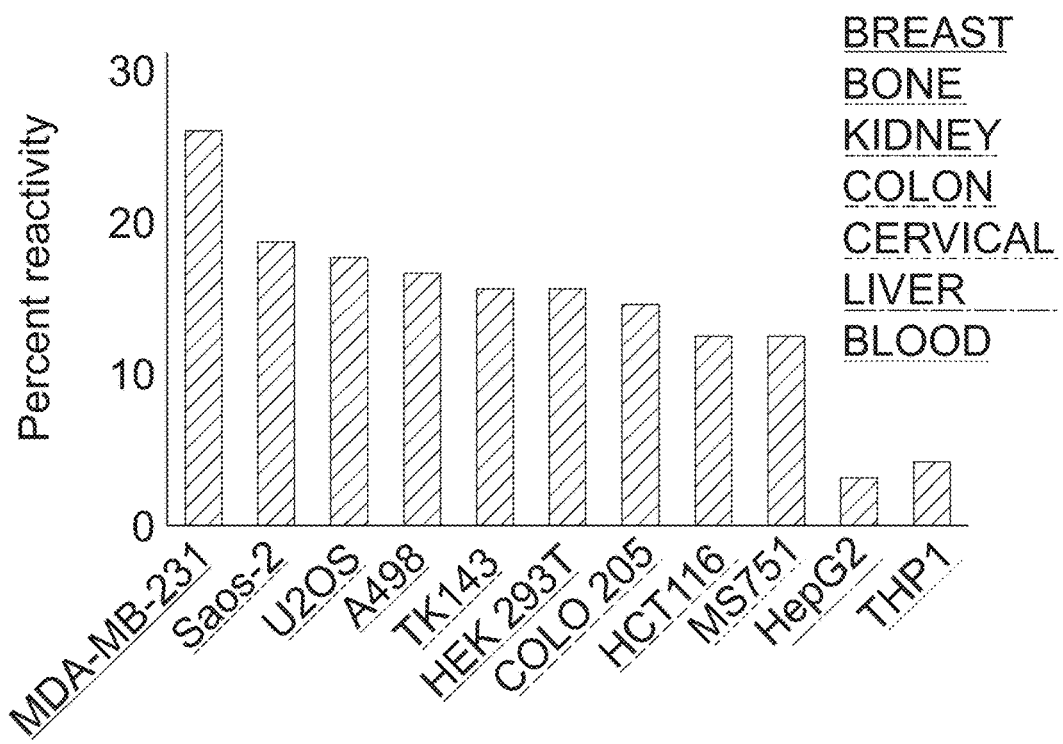
Figure 4C

Key:
Melan A (residues 26-35)
EAAGIGILTV
BST2 (residues 22-31)
LLLGIGILVL
IMP2 (residues 367-376)
NLSALGIFST Wild-type  MPREDAHFIYGYPKKGHGHSYTTAEEAAGIGILTVILGVLLLIGCWYCRRRNGYRALMD
KSLHVGTQCALTRRCPQEGFDHRDSKVSLQEKNCEPVVPNAPPAYEKLSAEQSPPPYSP Melan A KO  MPREDAHFIYGYPKKGHGHSYN*RGStop*

No stain
Secondary Ab alone
Melan A Ab + secondary Ab

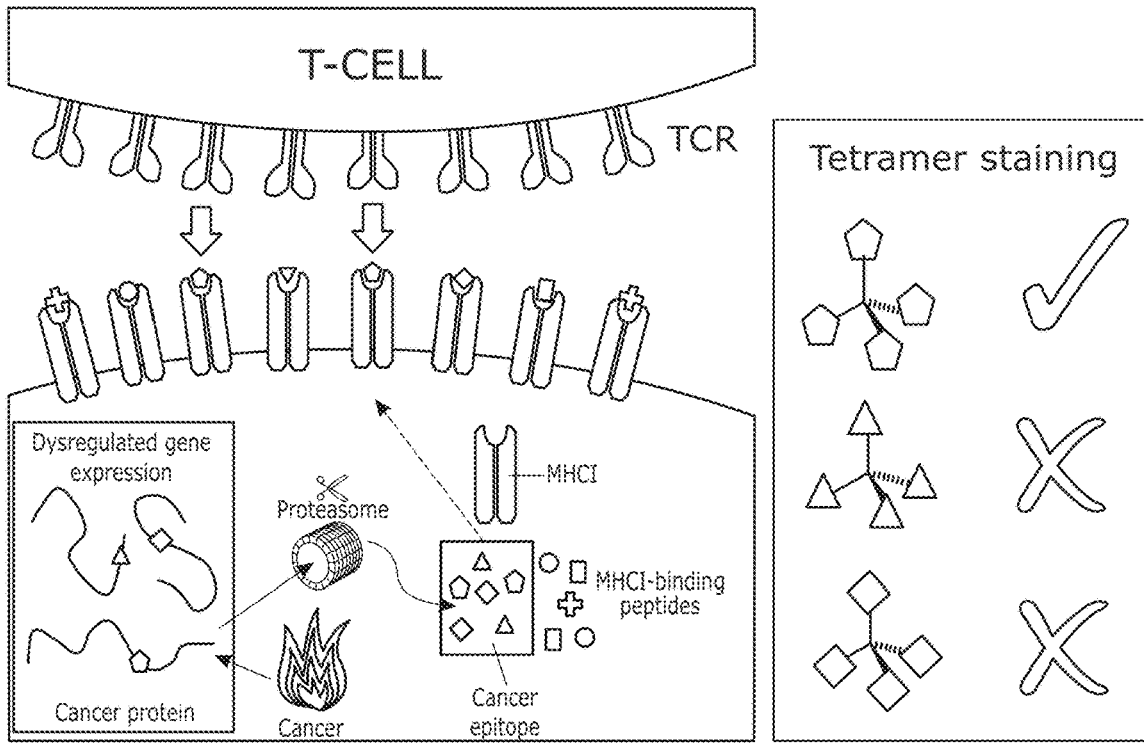
Figure 13A Normal Cancer-specific T-cell (recognizes one cancer peptide)
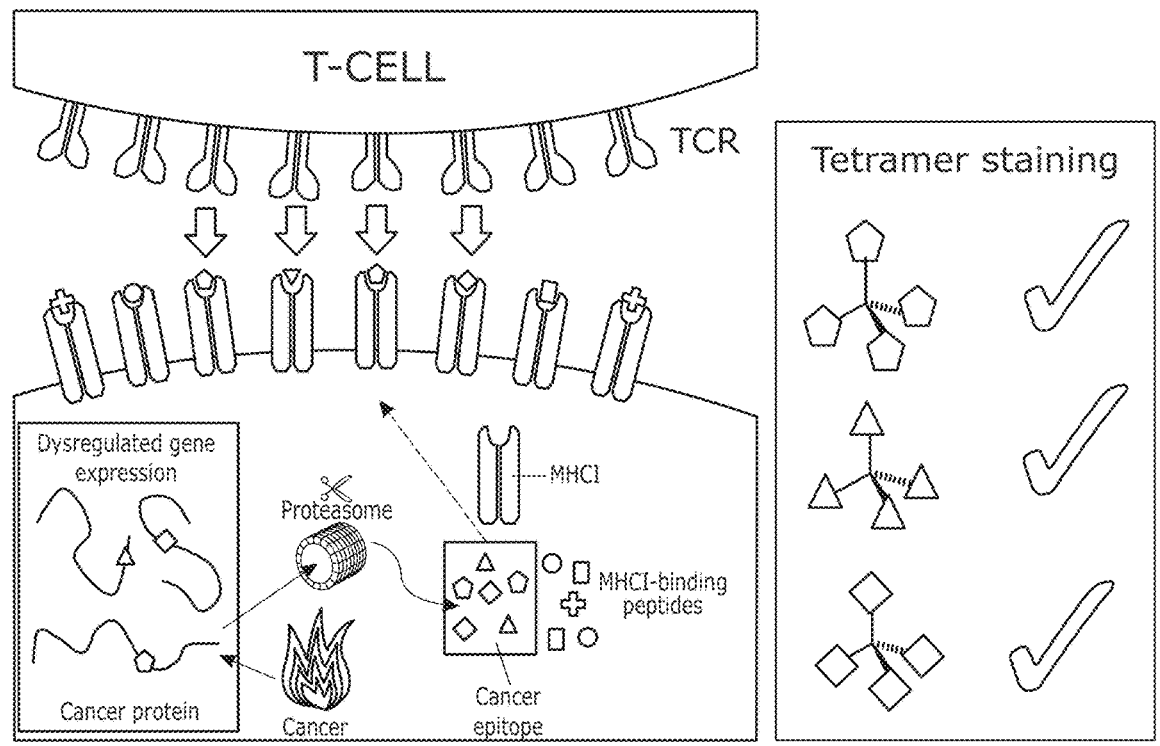
Figure 13B Multipronged Cancer-specific T-cell (recognizes more than one cancer peptide)

Multipronged T-cells recognise a *plurality* of different peptides derived from *different* cancer-specific antigens at the surface of the same cancer cell

Standard cross-reactive T-cell

A single T-cell/T-cell receptor recognises *different* peptides on the surface of different target cells

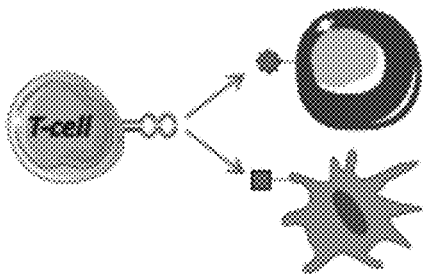

EXAMPLES

1. Autoimmune disease

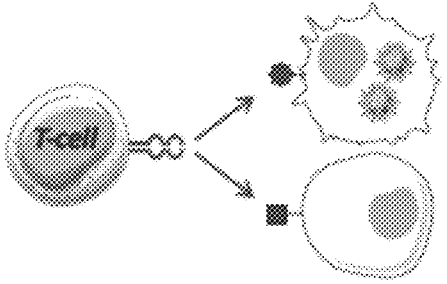

A pathogen-specific T-cell cross-reacts with a self peptide on a healthy cell via "molecular mimicry"

2. Heterologous Immunity

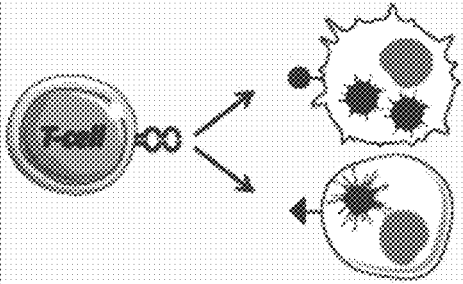

A T-cell specific for a peptide from one pathogen cross-reacts with a peptide from a different pathogen

Multipronged T-cell

Multipronged T-cells are rarer T-cells that recognise multiple different peptides on the surface of the *same* diseased cell. There are no known examples and such recognition has never even been suggested before

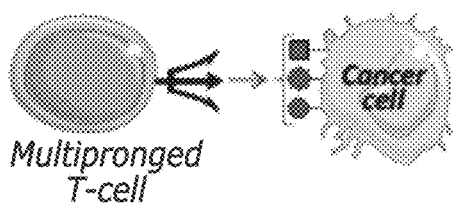
*Multipronged T-cell*

*Multipronged T-cell*

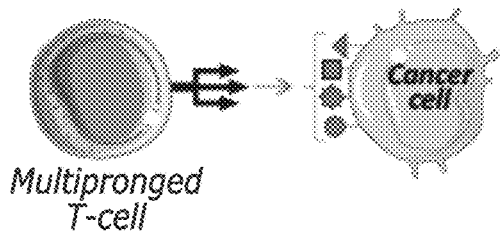
*Multipronged T-cell*

Multipronged T-cell Receptors

- Escape difficult [impossible?]
- More sensitive
- Less T-cells required
- More tumour types recognised

Figure 15

CANCER-SPECIFIC T-CELL RECEPTORS

RELATED APPLICATIONS

This application is a 35 U.S.C. § 371 filing of International Patent Application No. PCT/GB2019/051785, filed Jun. 25, 2019, which claims priority to Great Britain Patent Application No. 1810358.0, filed Jun. 25, 2018, the entire disclosures of each of which are hereby incorporated herein by reference.

SEQUENCE LISTING

The instant application contains a Sequence Listing in .txt. format which has been submitted via EFS-Web and is herein incorporated by reference in its entirety. The Sequence Listing, created on Nov. 20, 2023 is named 2023-11-20 CFF-P2730US-Amended sequence listing .txt and is 17766 bytes in size.

TECHNICAL FIELD

The present disclosure relates to a new anti-cancer peptide; a vector encoding same; a pharmaceutical composition or immunogenic agent or bispecific or vaccine comprising said anti-cancer peptide; use of said anti-cancer peptide, vector, pharmaceutical composition, immunogenic agent, bispecific or vaccine to treat cancer; a method of treating cancer using said anti-cancer peptide, vector, pharmaceutical composition, immunogenic agent, bispecific or vaccine; and a combination therapeutic for the treatment of cancer comprising said anti-cancer peptide, vector, pharmaceutical composition, immunogenic agent, bispecific or vaccine.

BACKGROUND

We have discovered a new class of T-cells effective for treating cancer.

It is established thinking that T-cells recognise individual cancer peptides through their cognate T-cell receptor. Thus, it has been thought that a single TCR recognises a single cancer antigenic peptide typically when presented at the cell surface in the context of human leukocyte antigen (HLA) class I or class II molecule.

This new work presented herein remarkably and significantly shows some T-cells recognise different cancer antigenic peptides (of distinct sequence) using the same T-cell receptor (TCR) thus indicating that a single TCR has the ability to recognise multiple and distinct cancer antigens. This is a unique finding that goes against conventional wisdom and has significantly beneficial implications in the treatment of cancer which is thought to be a multifaceted disease.

Our work shows these T-cells can recognise multiple, distinct peptides that are derived from different cancer antigens when presented at the cell surface in the context of the same human leukocyte antigen (HLA) class I molecule. In most cases the peptides are presented at the surface of the same cancer cell, which has not been described before.

It therefore appears that some rare T-cells are capable of recognising a range of individual cancer antigenic peptides through their cognate T-cell receptor. This novel type of T-cell utilises an identical T-cell receptor (TCR) to recognise cancer cells via multiple different cancer peptides. We have termed these T cells "multipronged T-cells" which, using their cognate TCR, can recognise and attack cancer cells via more than one antigen and thereby vastly reduce the chances of immune escape by cancer cells.

In 2015 about 90.5 million people had cancer. About 14.1 million new cases occur a year (not including skin cancer other than melanoma). It causes about 8.8 million deaths (15.7%) of human deaths. The most common types of cancer in males are lung cancer, prostate cancer, colorectal cancer and stomach cancer. In females, the most common types of cancer are breast cancer, colorectal cancer, lung cancer and cervical cancer. If skin cancer, other than melanoma, were included in total new cancers each year it would account for around 40% of cases. In children, acute lymphoblastic leukaemia and brain tumours are most common except in Africa where non-Hodgkin lymphoma occurs more often. In 2012, about 165,000 children under 15 years of age were diagnosed with cancer. The risk of cancer increases significantly with age and many cancers occur more commonly in developed countries. Rates are increasing as more people live to an old age and as lifestyle changes occur in the developing world. The financial costs of cancer were estimated at $1.16 trillion USD per year as of 2010. It follows that there is a need to provide better and safer ways of treating or eradicating this disease. An immunotherapy that uses the body's natural defence systems to kill aberrant tissue is acknowledged to be safer than chemical intervention but, to be effective, the immunotherapy must be able to clear the disease. Moreover, the discovery of an immunotherapy that is effective against any type of cancer or a number of cancers would be extremely beneficial as not only could it be administered to individuals suffering from many different types of cancer (i.e. it would have pan-population application) but it could also be administered to a single individual suffering from more than one type of cancer.

The T-cells and their receptors we have identified herein have the afore advantageous characteristics in that they are effective against more than one type of cancer thus safeguarding against a cancer evading the effectiveness of the immune system. Further, the production of these advantageous T cells and their receptors can be brought about by the use of the new anti-cancer peptides described herein.

STATEMENTS OF INVENTION

According to a first aspect of the invention there is provided an isolated anti-cancer T-cell receptor (TCR), or a fragment thereof, that recognises a plurality of cancer peptide antigens when said antigens are presented at a cell surface by human leukocyte antigen (HLA) class I molecule and wherein said antigens are distinct from each other and are representative of more than one type of cancer.

According to a further aspect of the invention there is provided an anti-cancer TCR or a cancer specific TCR, or a fragment thereof, that recognises a plurality of cancer antigens wherein said TCR has a complementarity-determining region selected from the group comprising or consisting of:

CATSDRGQGANWDEQFF;         (SEQ ID NO: 1)

CASTLGGGTEAFF;             (SEQ ID NO: 2)

CSARDLLAETYEQYF;           (SEQ ID NO: 3)

CASSSSDTDTQYF;             (SEQ ID NO: 4)

CSVEGSLGRALRANEQFF;           (SEQ ID NO: 5)

CATHGGEKLFF;                  (SEQ ID NO: 6)

CASSYVGLGSPLHF;               (SEQ ID NO: 7)

CSGQANTEAFF;                  (SEQ ID NO: 8)

CASSPTTGLKTRSGYTF;            (SEQ ID NO: 9)

CSEGSPYNEQFF;                 (SEQ ID NO: 10)

CASSNGFHFNTLYF;               (SEQ ID NO: 11)

CASSLGGGDTQYF;                (SEQ ID NO: 12)

CASSFAGTDTQYF;                (SEQ ID NO: 13)

CASSLGEGSPGELFF;              (SEQ ID NO: 14)

CASSQEPNWNTEAFF;              (SEQ ID NO: 15)

CASSFQGPGYGYTF;               (SEQ ID NO: 16)

CSARDTTWGLEQYF;               (SEQ ID NO: 17)

CATKPSGSTDTQYF;               (SEQ ID NO: 18)

CSARDEGIGYEQYF;               (SEQ ID NO: 19)

CASSSGPGELFF;                 (SEQ ID NO: 20)

CARRTLVIVRRFYSGNTIYF;         (SEQ ID NO: 21)

CSARDLIGSQTYEQYF;             (SEQ ID NO: 22)

CSARDPIGTESYEQYF;             (SEQ ID NO: 23)

CSARDRAGRSPLHF;               (SEQ ID NO: 24)

CSVEESSGIYEQYF;               (SEQ ID NO: 25)

CSAREDGGQTYEQYF;              (SEQ ID NO: 26)

CASSWAGPVEQYF;                (SEQ ID NO: 27)

CASSSQGRAEQYF;                (SEQ ID NO: 28)

CASSSRDSLYEQYF;               (SEQ ID NO: 29)

CASSLGIISGQPQHF;              (SEQ ID NO: 30)

CASSNTGGYTQYF;                (SEQ ID NO: 31)

CASSQGLLLDNEQFF;              (SEQ ID NO: 32)

CASSSPMDSGDTDTQYF;            (SEQ ID NO: 33)

CASSPRSGVPQHF;                (SEQ ID NO: 34)

CASSFVREEGSTDTQYF;            (SEQ ID NO: 35)

CSARGTESYEQYF;                (SEQ ID NO: 36)

CASWPGEGFGETQYF;              (SEQ ID NO: 37)

CSGWGQGDEKLFF;                (SEQ ID NO: 38)

CASSEYTSGNQPQHF;              (SEQ ID NO: 39)

CSARDLWTGETYEQYF;             (SEQ ID NO: 40)

CSATGLAGLGEQFF;               (SEQ ID NO: 41)

CATSDLGTGVGEQFF;              (SEQ ID NO: 42)

CSVGPGSTGELFF;                (SEQ ID NO: 43)

CASSPTGEKLFF;                 (SEQ ID NO: 44)

CASSQEGGTWGDGYTF;             (SEQ ID NO: 45)

CATSDLLLAGGRSSYNEQFF;         (SEQ ID NO: 46)

CASSEAASGRPQTF;               (SEQ ID NO: 47)

CATSDATAGTSGSLYEQYF;          (SEQ ID NO: 48)

CASSLTGLGQPQHF;               (SEQ ID NO: 49)

CASSPAVLSYEQYF;               (SEQ ID NO: 50)

CSARESLAETYEQYF;              (SEQ ID NO: 51)

CASSPGLTANVLTF;               (SEQ ID NO: 52)

CASSLGLAGNEQYF;               (SEQ ID NO: 53)

CASSNGFHFNTQYF;               (SEQ ID NO: 54)

CASSLGILTDTQYF;               (SEQ ID NO: 55)

CASSFQPVDTQYF;                (SEQ ID NO: 56)

```
CSASEGIGQPQHF;
                                     (SEQ ID NO: 57)

and

CASSVSGGEQFF.,
                                     (SEQ ID NO: 58)
``` or a complementarity-determining region that has at least 85% identity with any one or more of the afore complementarity-determining regions.

In a further preferred embodiment said complementarity-determining region has at least 86, 87, 88, 89, 90, 91, 92, 93, 94, 95, 96, 97, 98 or 99% identity with any one or more of the afore complementarity-determining regions.

In a preferred embodiment of the invention said plurality of antigens are presented at the cell surface in the context of human leukocyte antigen (HLA) class I molecule and, more preferably still, said recognition occurs or is shown to occur by any one or more of, including any combination of, the following activities:

- said TCR, or a T cell expressing said TCR, triggers or causes death of a cancer cell expressing any one or more of said antigens; and/or
- said TCR, or a T cell expressing said TCR, triggers the production of or makes pro-inflammatory cytokines such as TNF and IFN gamma (this feature is useful for reversing the immunosuppressive tumour microenvironment); and/or
- said TCR, or a T cell expressing said TCR, triggers degranulation or undergoes degranulation; and/or
- said TCR, or a T cell expressing said TCR, upregulates any one or more of CD107a, Beta-chemokines (MIP 1 beta) and cytokines such as Interferon gamma (IFN-gamma) and tumour necrosis factor (TNF).

In a preferred embodiment of the invention said TCR has a complementarity-determining region selected from the group comprising or consisting of:

```
CATSDRGQGANWDEQFF;                   (SEQ ID NO: 59)

CASTLGGGTEAFF;                       (SEQ ID NO: 60)

CSARDLLAETYEQYF;                     (SEQ ID NO: 61)

CASSSSDTDTQYF;                       (SEQ ID NO: 62)

CSVEGSLGRALRANEQFF;                  (SEQ ID NO: 63)

CATHGGEKLFF;                         (SEQ ID NO: 64)

CASSYVGLGSPLHF;                      (SEQ ID NO: 65)

CSGQANTEAFF;                         (SEQ ID NO: 66)

CASSPTTGLKTRSGYTF;                   (SEQ ID NO: 67)

CSEGSPYNEQFF;                        (SEQ ID NO: 68)

CASSNGFHFNTLYF;                      (SEQ ID NO: 69)
and

CASSLGGGDTQYF;                       (SEQ ID NO: 70)
``` or a complementarity-determining region that has at least 85% identity with any one or more of the afore complementarity-determining regions.

In a further preferred embodiment said complementarity-determining region has at least 86, 87, 88, 89, 90, 91, 92, 93, 94, 95, 96, 97, 98 or 99% identity with any one or more of the afore complementarity-determining regions.

In a preferred embodiment of the invention said more than one types of cancer are selected from the group comprising or consisting of: nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, tonsil, spleen, neuroma, von Hippel-Lindau disease, Zollinger-Ellison syndrome, adrenal cancer, anal cancer, bile duct cancer, bladder cancer, ureter cancer, glioma, oligodendroglioma, neuroblastoma, meningioma, spinal cord tumour, bone cancer, osteochondroma, chondrosarcoma, Ewing's sarcoma, cancer of unknown primary site, carcinoid, carcinoid of gastrointestinal tract, fibrosarcoma, breast cancer, muscle cancer, Paget's disease, cervical cancer, ovarian, blood, colon cancer, rectal cancer, oesophagus cancer, gall bladder cancer, cholangioma cancer, head cancer, eye cancer, nasopharynx cancer, neck cancer, kidney cancer, Wilms' tumor, liver cancer, Kaposi's sarcoma, prostate cancer, testicular cancer, Hodgkin's disease, non-Hodgkin's lymphoma, skin cancer, mesothelioma, myeloma, multiple myeloma, ovarian, endocrine, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In yet a further preferred embodiment of the invention said more than one types of cancer are selected from the group comprising or consisting of: pancreatic, blood, ovarian, skin, breast, cervical, prostate, bone, lung, liver, colon and kidney.

Reference herein to cancer antigens that are distinct from each other is reference to cancer antigens that are representative of different types of cancer and so reference to antigens that are distinctly different in terms of their sequence structure or the molecule, typically protein, from which they are derived.

Nevertheless, despite this difference in antigen sequence the TCR of the invention is able to recognise a plurality of these distinct or different cancer antigens. Those skilled in the art will appreciate, it would be extremely difficult for cancer cells to escape from T-cells that were targeting them through more than one different cancer antigen as escape would require simultaneous mutation of all targets that lowered or ablated presentation of all cognate peptides.

In a preferred embodiment of the invention said human leukocyte antigen (HLA) class I molecule is MHC class I (A, B, or C). More specifically, said HLA is HLA A2 or HLA A24 or HLA A1 or HLA A3.

MHC class I present peptides from inside the cell. For example, in the context of a cancer cell, the HLA system brings fragments or peptides of the cancer-expressed protein to the surface of the cell so that the cell can be recognised as cancerous and destroyed by the immune system. These peptides are produced from digested proteins that are broken down in the proteasomes. In general, these particular peptides are small polymers, about 7-20, typically but not exclusively 9 or 10 amino acids in length. Oncogenic antigens presented by MHC class I system attract killer T-cells (also called CD8 positive- or cytotoxic T-cells) that destroy the cancer cells.

In a preferred embodiment of the invention said TCR is an alpha beta (αβ) TCR.

In yet a further preferred embodiment, said TCR is a soluble TCR (sTCR) and so lacks the transmembrane and, ideally also, intracellular domains.

In yet another preferred embodiment of the invention said TCR is part of a chimeric receptor having the functionality described herein. Ideally, said TCR is fused to a TCR constant domain or a TCR signalling domain.

In the alternative, there is provided a fragment of said TCR such as a monomeric part thereof, ideally a single chain form of the TCR.

In a further alternative, there is provided a fragment of said TCR such as the complementarity determining region thereof.

According to a further aspect of the invention there is provided a T-cell expressing said TCR of the invention, ideally, in either a soluble form or membrane compatible form i.e. having a transmembrane region and intracellular region.

According to a yet further aspect of the invention there is provided a T-cell clone expressing said TCR of the invention, ideally, in either a soluble form and so lacks a transmembrane domain and, ideally also, an intracellular domain or a membrane compatible form i.e. having a transmembrane region and, ideally also, an intracellular domain.

Preferably said clone is a T-cell clone CR24, GD1, GD2, VB6G4.24, CR1 or VB10 as described herein.

Ideally, said clone is CR24 which recognises multiple antigenic cancer peptides, most preferably clone CR24 recognises a plurality of said peptides selected from the group comprising or consisting of: EAAGIGILTV (SEQ ID NO: 71) from Melan A (residues 26-35), LLLGIGILVL (SEQ ID NO: 72) from BST2 (residues 22-31) and NLSALGIFST (SEQ ID NO: 73) from IMP2 (residues 367-376). Preferably, this recognition is in the context of HLA A2 presentation.

Ideally, said clone GD1 or GD2 recognises multiple antigenic cancer peptides, most preferably clone GD1 or GD2 recognises the following peptides: RLVDDFLLV (SEQ ID NO: 74) from human telomerase reverse transcriptase (hTERT) (residues 855-873) and ALKDVEERV (SEQ ID NO: 75) from melanoma associated antigen C2 (MAGE C2) (residues 336-344). Clone GD1 was able to kill breast, blood and melanoma cancer cell lines.

Ideally, said clones VB6G4.24, CR1 and VB10 recognise the Melan A peptide (EAAGIGILTV (SEQ ID NO: 71)) but not BST2 (LLLGIGILVL (SEQ ID NO: 72) or IMP2 (NLSALGIFST (SEQ ID NO: 73)) peptides (neither as exogenous peptide nor from transduced protein expressed by MOLT3s). Since the CDR3 sequence of the beta TCR chain from VB6G4.24 appeared in clonotyping data for all ten cancer cell lines in FIGS. 2A-2B, this clone responds to multiple cancer cells lines but not by recognition of the IMP2 or BST2 peptides.

According to a yet further aspect of the invention there is provided a vector encoding said TCR of the invention.

According to a yet further aspect of the invention there is provided a pharmaceutical composition or immunogenic agent or bispecific or vaccine comprising said TCR or T-cell or T-cell clone or vector of the invention.

In a preferred embodiment said pharmaceutical composition or immunogenic agent or bispecific or vaccine is for use in the treatment of cancer.

According to a yet further aspect of the invention there is provided the TCR or T-cell or T-cell clone or vector as disclosed herein for use in the treatment of cancer.

According to a yet further aspect of the invention there is provided a method of treating cancer in an individual having or suspected of having cancer comprising administering said TCR or T-cell or T-cell clone or vector or pharmaceutical composition or immunogenic agent or bispecific or vaccine to the individual to be treated.

Ideally said cancer is of any type. More ideally, said cancer is selected from the group comprising or consisting of: nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, tonsil, spleen, neuroma, von Hippel-Lindau disease, Zollinger-Ellison syndrome, adrenal cancer, anal cancer, bile duct cancer, bladder cancer, ureter cancer, glioma, oligodendroglioma, neuroblastoma, meningioma, spinal cord tumour, bone cancer, osteochondroma, chondrosarcoma, Ewing's sarcoma, cancer of unknown primary site, carcinoid, carcinoid of gastrointestinal tract, fibrosarcoma, breast cancer, muscle cancer, Paget's disease, cervical cancer, ovarian, blood, colon cancer, rectal cancer, oesophagus cancer, gall bladder cancer, cholangioma cancer, head cancer, eye cancer, nasopharynx cancer, neck cancer, kidney cancer, Wilms' tumor, liver cancer, Kaposi's sarcoma, prostate cancer, testicular cancer, Hodgkin's disease, non-Hodgkin's lymphoma, skin cancer, mesothelioma, myeloma, multiple myeloma, ovarian, endocrine, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

Most preferably said cancer is pancreatic, blood, ovarian, skin, breast, bone, kidney, colon, cervical, liver, prostate or lung cancer.

In a preferred method of the invention said TCR, cell, clone or vector is administered in combination with an anti-cancer agent such as, but not limited to, a bispecific antibody.

Reference herein to a bispecific is reference to a bispecific monoclonal antibody (BsMAb, BsAb) which is an artificial protein that can simultaneously bind to two different types of antigen.

Alternatively still, said TCR may form part of a Bispecific antibody wherein said bispecific includes said TCR, for the purpose of binding to its ligand on a cancer cell, and also an immune cell activating component or ligand that binds and so activates an immune cell such as a Killer T-cell.

According to a yet further aspect of the invention there is provided the use of said TCR or cell or clone or vector in the manufacture of a medicament to treat cancer.

According to a yet further aspect of the invention there is provided a combination therapeutic for the treatment of cancer comprising:
a) said TCR or cell or clone or vector or immunogenic agent or bispecific or vaccine in combination with
b) a further cancer therapeutic agent.

According to a yet further aspect of the invention there is provided an anti-cancer peptide or peptide antigen able to elicit anti-cancer T-cells, which, ideally but not exclusively, recognises said TCR of the invention, or a part thereof, and which when administered to a subject primes the production of: anti-cancer T-cells that act as effector T-cells and/or T-cells that recognise a plurality of cancer antigens when said peptide antigens are presented at a cell surface by human leukocyte antigen (HLA) class I molecule and wherein said cancer antigens are distinct from each other and are representative of more than one type of cancer.

According to a further aspect or in a preferred embodiment an/said anti-cancer peptide is selected from the group comprising or consisting of:

ITSAIGVLPV; (SEQ ID NO: 76)

ITSAIGILPV; (SEQ ID NO: 77)

MTSAIGVLPV; (SEQ ID NO: 78)

QTSAIGVLPV; (SEQ ID NO: 79)

MTSAIGILPV; (SEQ ID NO: 80)

LTSAIGVLPV; (SEQ ID NO: 81)

ITSGIGVLPV; (SEQ ID NO: 82)

ITSAIGVLPI; (SEQ ID NO: 83)

QTSAIGILPV; (SEQ ID NO: 84)

ITSAIGVLFV (SEQ ID NO: 85)

Most ideally, said anti-cancer peptide is MTSAIGILPV. More ideally still said peptide has 80% or 90 identity with one of the afore peptides and so includes one or two substitutions. deletions or additions.

According to a further aspect of the invention there is provided a vaccine comprising said anti-cancer peptide.

According to a further aspect of the invention there is provided a pharmaceutical composition or immunogenic agent or bispecific comprising said anti-cancer peptide.

According to a further aspect of the invention there is provided a method of treating cancer comprising administering the anti-cancer peptide, in its native form or as a vaccine, pharmaceutical composition, immunogenic agent or bispecific, to a subject.

According to a further aspect of the invention there is provided the use of an anti-cancer peptide for use in treating cancer.

According to a further aspect of the invention there is provide the use of the anti-cancer peptide in the manufacture of a medicament for treating cancer.

In a preferred embodiment of the invention said cancer is selected from those disclosed herein, especially skin cancer or melanoma.

In the claims which follow and in the preceding description of the invention, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

Figure 1B:
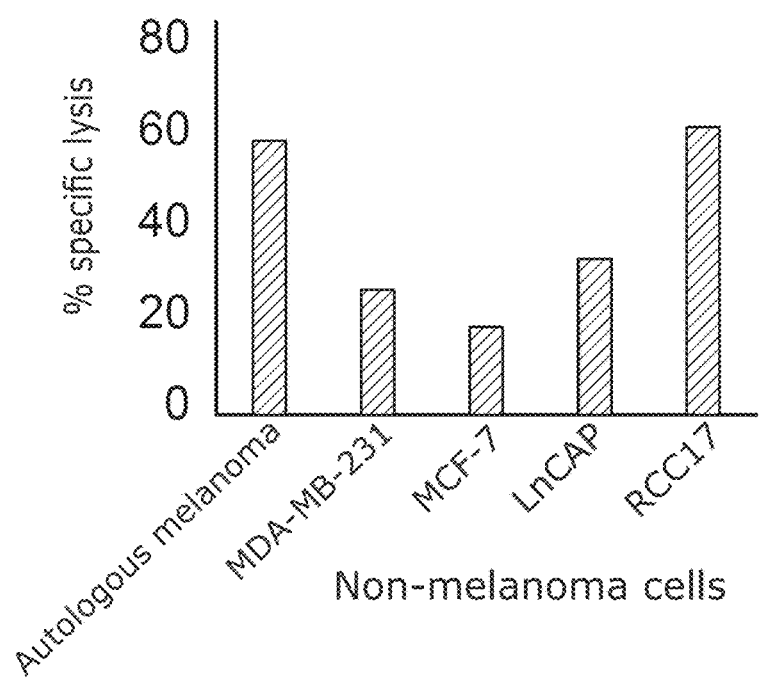
Figure 1C:
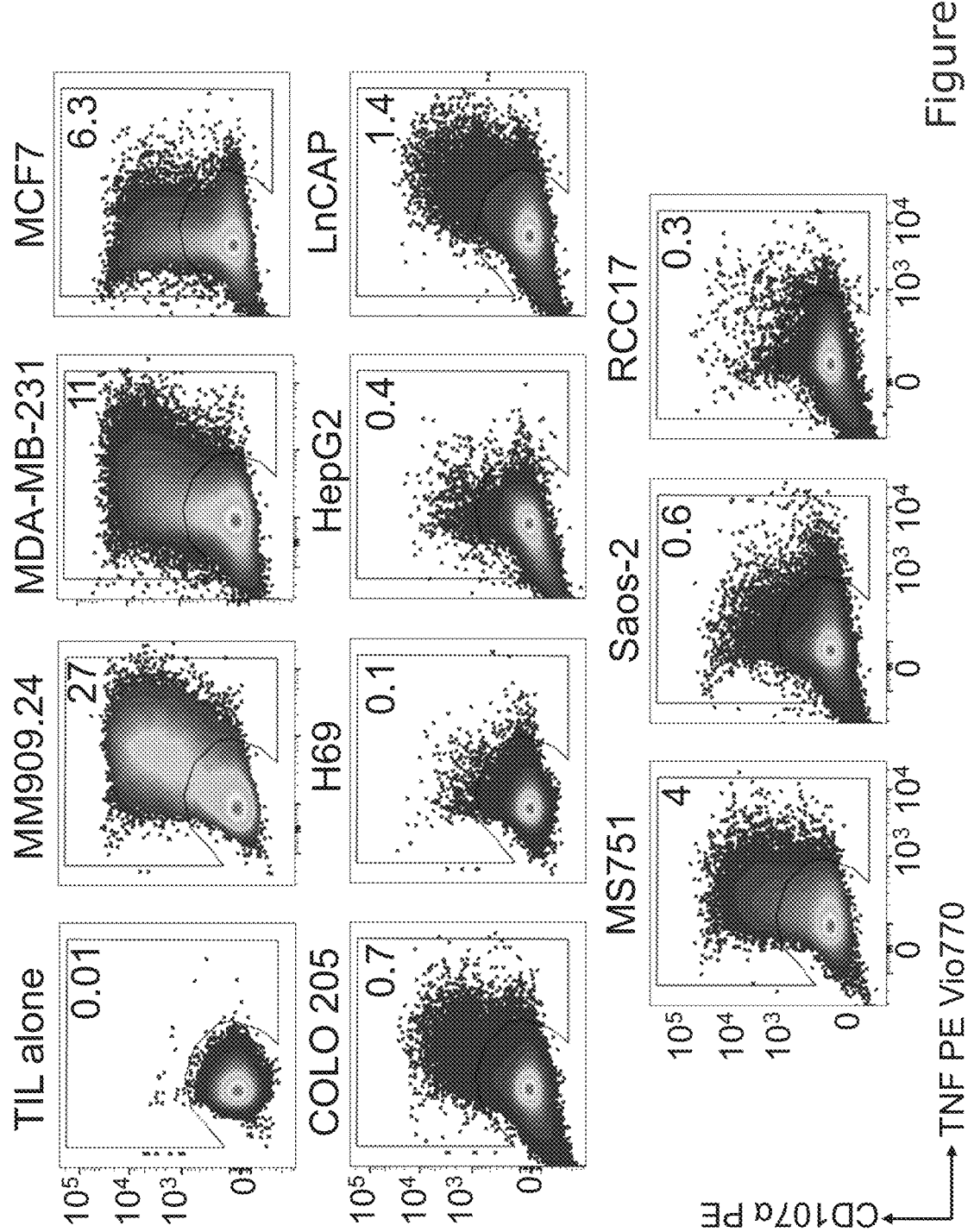

An embodiment of the present invention will now be described by way of example only with reference to the following wherein:

FIGS. 1A-1C show tumour infiltrating lymphocytes (TILs) used to cure HLA A2+ patient MM909.24 of metastatic melanoma are capable of recognising multiple HLA A2+ cancer cell types. (FIG. 1A) The TILs were tested against autologous melanoma and cancer cell lines of different tissue origin. (FIG. 1B) Chromium release cytotoxicity assay with autologous melanoma and the HLA A2+ cancer cell lines displayed. The cell lines are colour coded according to their tissue of origin (FIG. 1A). Specific lysis after 18 h of incubation is displayed. (FIG. 1C) TAPI-0 assay whereby TILs were incubated with the indicated HLA A2+ cancer cell lines for 5 h and activation assessed by detection of TNF and CD107a with monoclonal antibodies. The activated gate (TNF+ and/or CD107a+) was set based on the TIL alone control. Responding T-cells were sorted by flow cytometry and used for next generation sequencing of the α and β chains of the T-cell receptor (TCR).

Figure 2A:
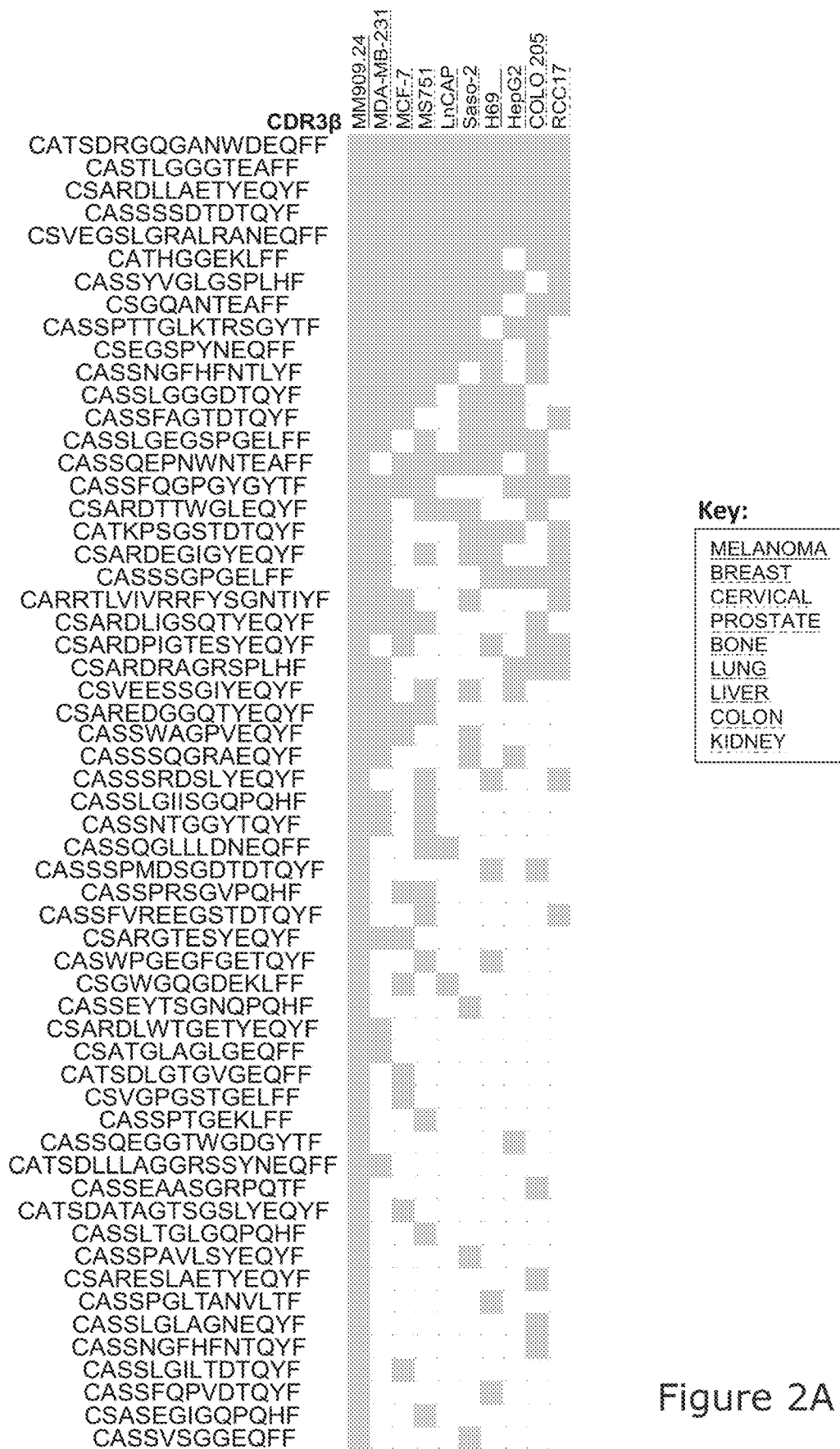
Figure 2B:
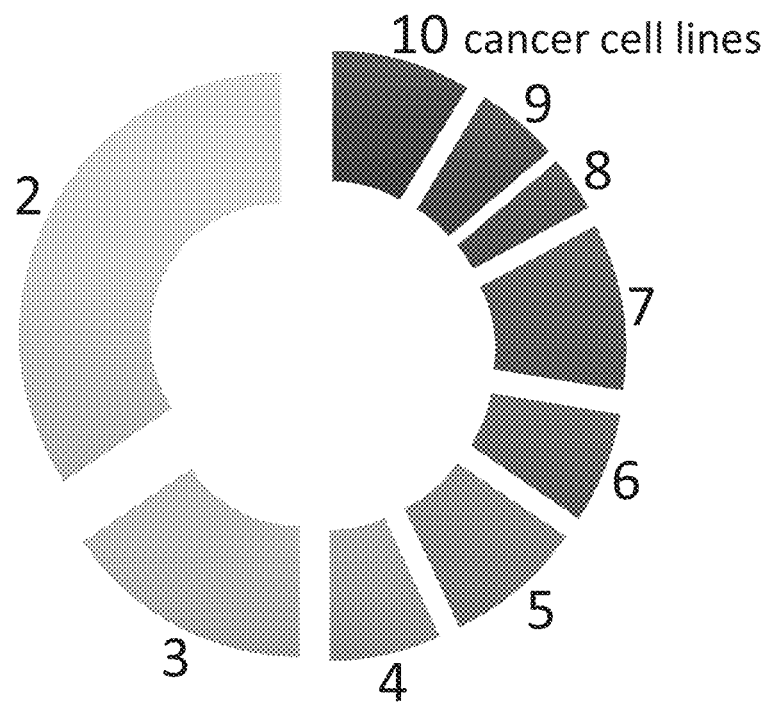

FIGS. 2A-2B show T-cell receptor (TCR) β chains clonotypes of functional T-cells, from the TIL of HLA A2+ patient MM909.24, able to respond to cancer cell lines as well as autologous melanoma (MM909.24). Cells were sorted based on function (TAPI-0 assay with CD107a and TNF antibodies) following 5 h of incubation with the HLA A2+ cancer cell lines shown (FIG. 1) and used for high throughout Illumina sequencing of the TCR chains. (FIG. 2A) The TCR β chain CDR3s of SEQ ID NOs: 1 to 58 are displayed on the left, with each shaded blue segment of the chart indicating that the CDR3 was present in the population responding to the cancer cell line shown at the top of the chart. Five TCRs are seen to respond to all cancers. (FIG. 2B) Shows the proportion of CDR3s that recognised the number of cancer cell lines shown next to each segment. For example; 2 cell lines=autologous melanoma+ one other cancer cell line; 10 cell lines=autologous melanoma+9 other cancer cell lines. Over 50% of the clonotypes that respond to HLA A2+ autologous melanoma also respond to 4 or more other cancer types.

FIGS. 3A-3D show a cancer epitope discovery pipeline. This figure depicts the strategy used to discover the peptide(s) recognised by T-cells that respond to multiple cancer cell types. (FIG. 3A) CD8 T-cells were cloned from TIL MM909.24 by limiting dilution then screened for cytotoxicity against autologous MM909.24 melanoma. In some cases, other cancer cell types were also used during the screening. Clones of interest were expanded and used for further assays. (FIG. 3B) Combinatorial peptide library screening was performed for key CD8 T-cell clones to reveal their amino acid residue preferences at each position of a peptide. The schematic shows the design of a CPL library, comprised of peptide sub-libraries; each sub-library has a fixed amino acid residue (open circle) (1 of the 20 proteogenic amino acids) at a defined position of the peptide, with all other positions of the same sub-library being a random mix of residues (grey square). (FIG. 3C) The CPL data (example shown in FIG. 5) was used to screen a cancer protein database (manuscript in preparation) to shortlist candidate peptides that are predicted to be recognised by the clone. (FIG. 3D) Functional testing of candidate cancer peptides to reveal those recognised by a CD8 clone.

FIGS. 4A-4C show T-cell cone CR24 can recognise multiple HLA A2+ cancer cell lines of different tissue origin. TAPI-0 assays were used to assess the reactivity of CR24 towards the cancer cell lines shown. The percentage of reactivity (CD107a+ and/or TNF+) is displayed. (FIG. 4A) CR24 recognised HLA A2+ melanomas but not HLA A2-negative melanomas. (FIG. 4B) The leukaemic cell line CIR was recognised when HLA A2 was expressed. (FIG. 4C) Recognition of non-melanoma HLA A2+ cell lines of different tissue origin (key).

Figure 5:
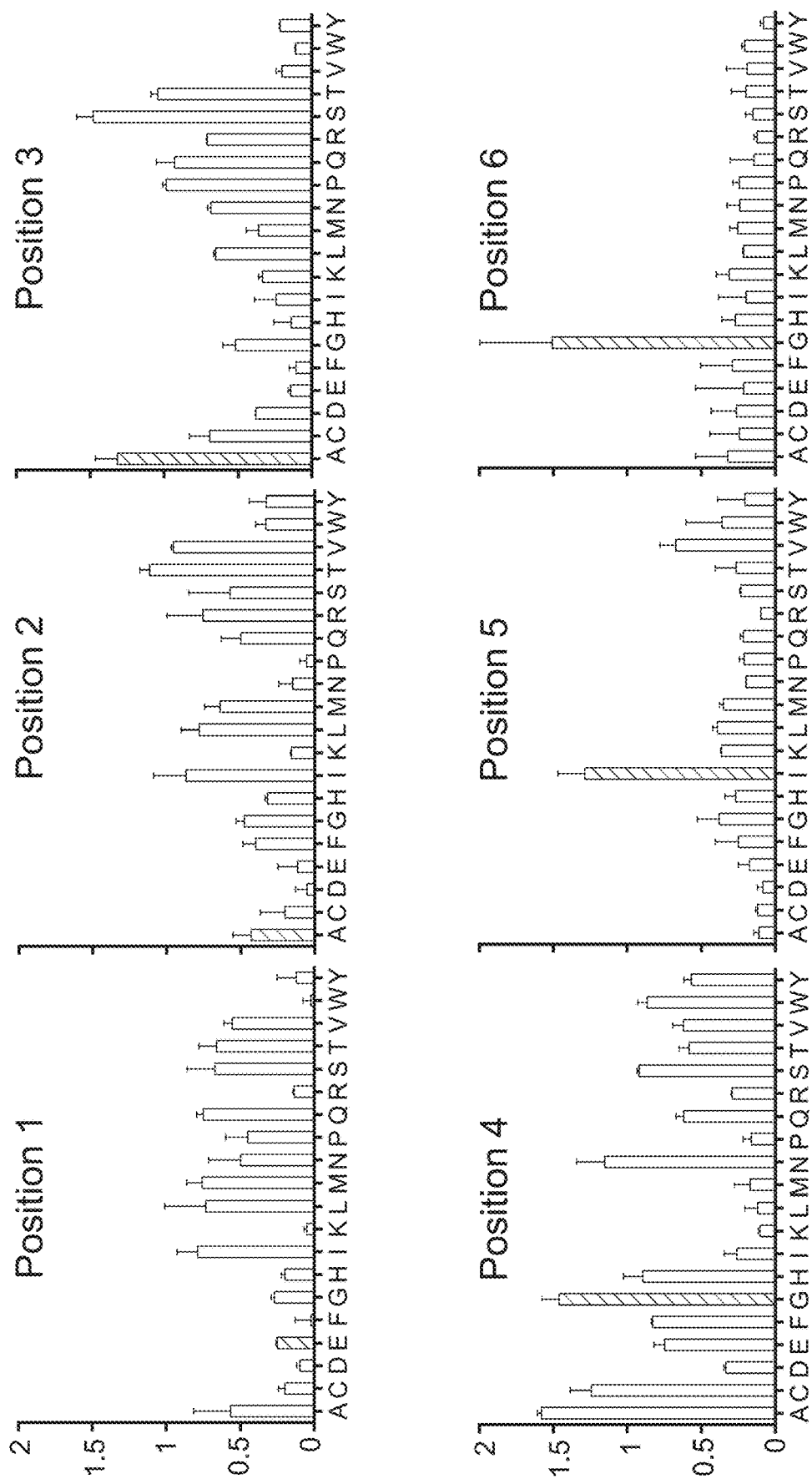
Figure 5:
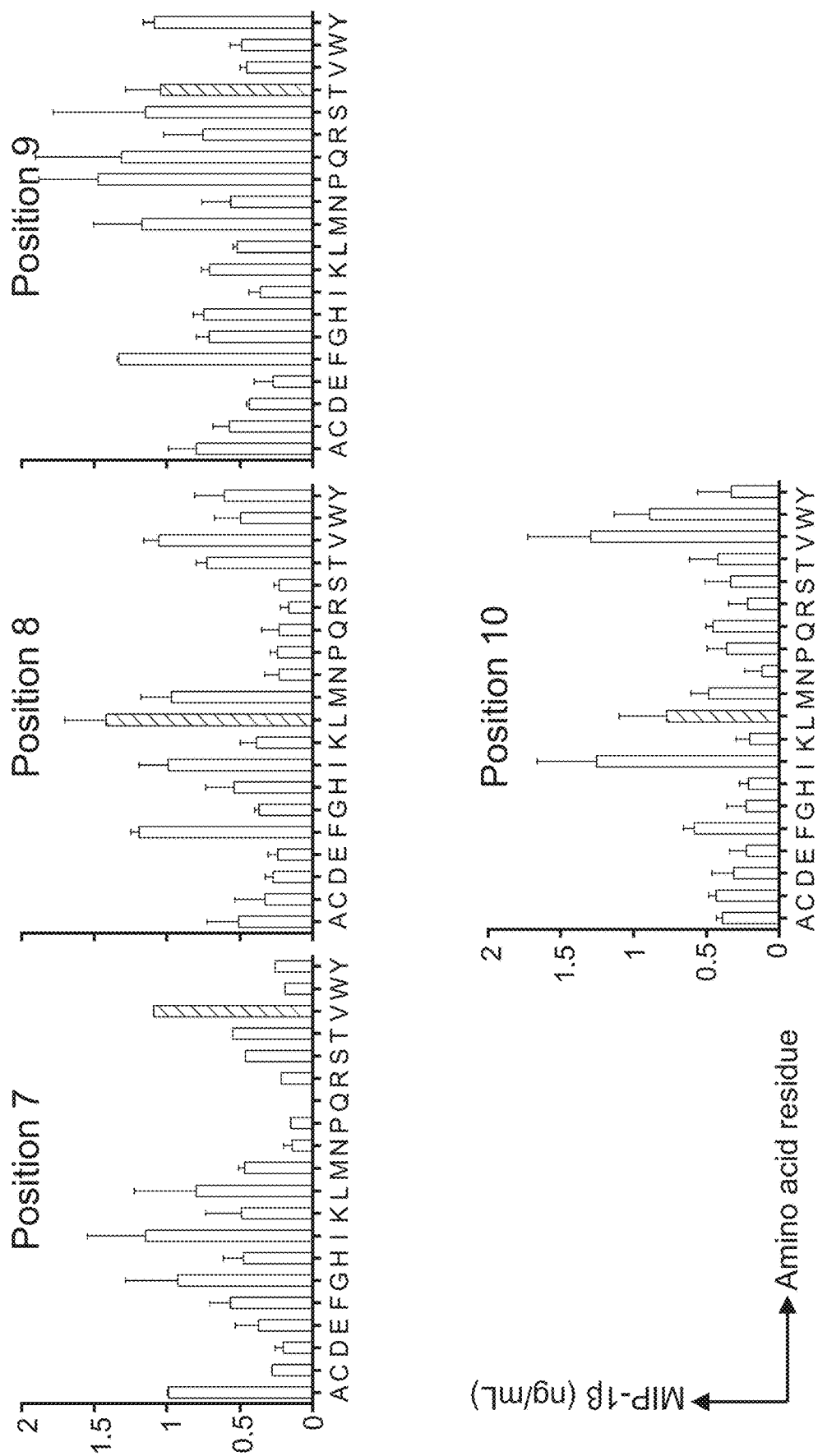

FIG. 5 shows combinatorial peptide library (CPL) screen of CD8 T-cell clone CR24. Each sub library of a decamer CPL screen was incubated in duplicate with CR24, with the TAP (transporter associated with antigen processing) deficient cell line T2 used as an antigen presenting cell. The peptide length (10mers) preference of CR24 had already been determined using a sizing scan assay (data not shown). After overnight incubation the supernatants were harvested, and clone activation assessed by MIP1-β ELISA. Each graph shows one peptide position of the CPL screen, with the amino acids (single letter code) shown on the x-axis fixed at that particular position. The bars in green show the amino acid residues for one of the peptides recognised by CR24, EAAGIGILTV (SEQ ID NO: 71 from Melan A (residues 26-35). The CPL data was run via a bespoke cancer antigen webtool to give candidate peptides that are most likely to be recognised by CR24 (FIGS. 6A-6C).

Figure 6A:
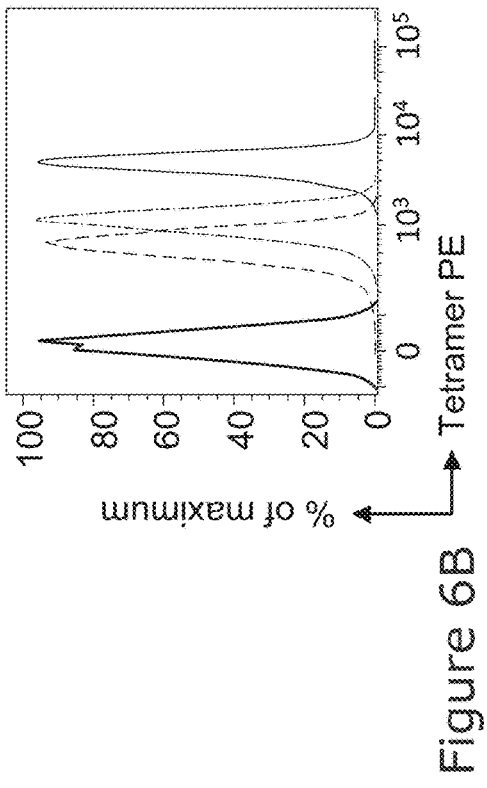
Figure 6B:
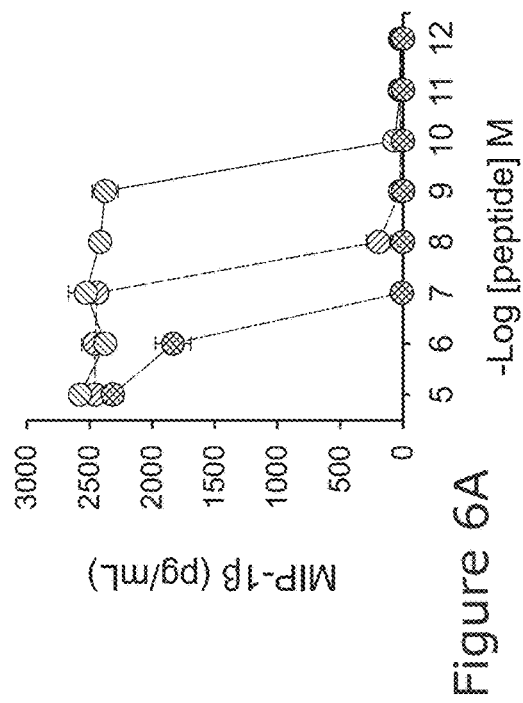
Figure 6C:
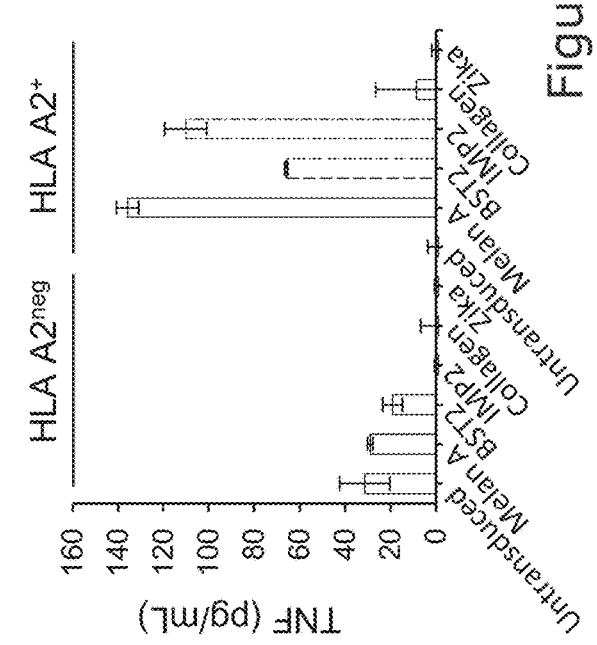
Figures 7A, 7B:
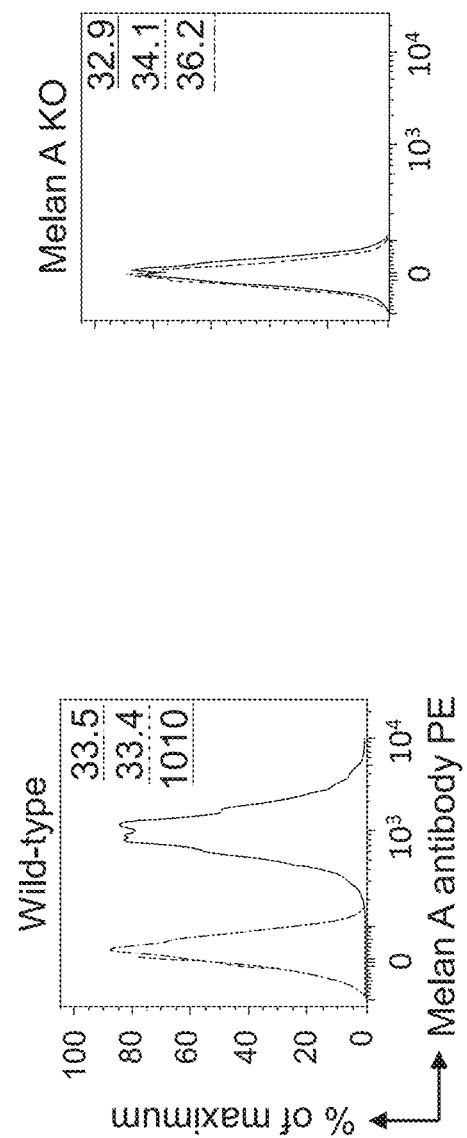
Figure 7C:
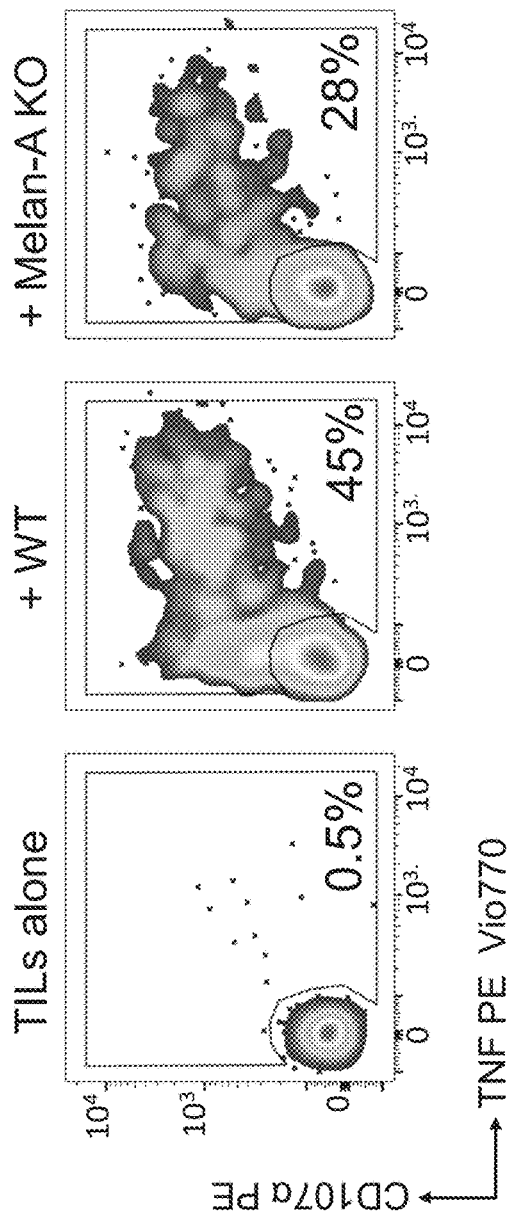
Figure 7D:
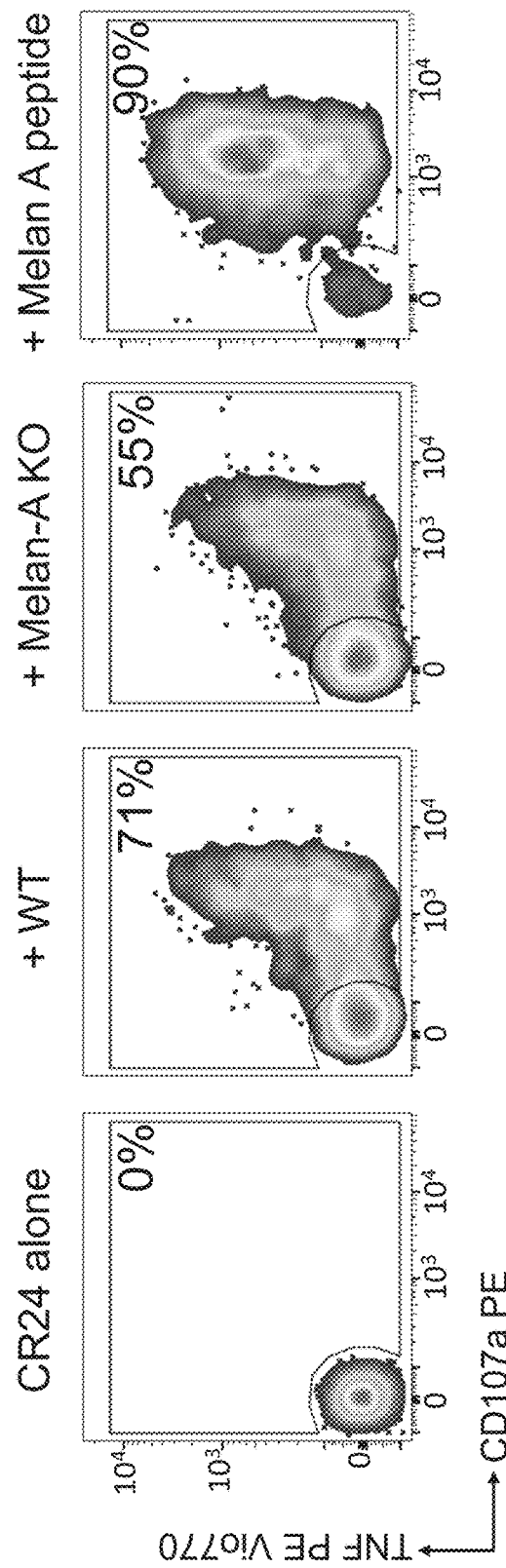

FIGS. 6A-6C show T-cell clone CR24 recognises three distinct peptides derived from different cancer proteins. Of the candidate peptides identified by the combinatorial peptide library screen performed in FIGS. 4A-4C, three of peptides were recognised by CR24; EAAGIGILTV (SEQ ID NO: 71, Melanoma Antigen Recognised by T-cells 1/Melanocyte Antigen (MART-1/Melan A, residues 26-35) iedb.org/epId/10987), LLLGIGILVL (SEQ ID NO: 72, Bone marrow stromal antigen 2 (BST2, residues 22-31) and NLSALGIFST from Insulin-like growth factor 2 mRNA binding protein 2 (SEQ ID NO: 73, IMP2, residues 367-376). The two amino acid residues common to all three peptides are shown in red in the key. The Melan A peptide is well described as a target of T-cells recognising melanomas. A 9-amino acid length version of the BST2 peptide has been described previously (10: ncbi.nlm.nih.gov/pubmed/16569595). The IMP2 peptide is a new epitope that has not previously been described (manuscript in preparation). (FIG. 6A) Activation assay with CR24 and a titration of each peptide, incubated overnight and supernatants used for MIP-1β ELISA. (FIG. 6B) CR24 stained with HLA A2 tetramers for each of the peptides confirming that the cognate TCR could engage these antigens. An optimised staining protocol was used. The control tetramer is HLA A2 ALWGPDPAAA (SEQ ID NO: 86, preproinsulin residues 15-24). (FIG. 6C) Activation assays with CR24 and antigen presenting cells expressing the proteins that the three cancer peptides are derived from. The cell line, MOLT3 (naturally HLA-A2 negative, Melan A negative, BST2 negative and IMP2 negative) were transduced with genes for expression of HLA A2, Melan A, BST2, IMP2, the α2 subunit of collagen type IV and the anchor capsid protein from Zika virus. The collagen and Zika proteins acted as transduction/irrelevant protein controls. CR24 was incubated overnight with each of the MOLT3 cell lines and supernatants harvested for TNF ELISA.

FIGS. 7A-7D show T-cell clone CR24 recognises autologous melanoma through at least two antigens. (FIG. 7A) The Melan A gene in autologous MM909.24 melanoma was targeted for ablation using a guide (g) RNA and CRISPR-Cas9. The wild-type Melan A amino acid sequence (SEQ ID NO: 87) is shown with the EAAGIGILTV (SEQ ID NO: 71) peptide in blue. Sequencing of the Melan A loci confirmed gene disruption due to an early STOP codon (red, SEQ ID NO: 88), at both alleles, which was downstream of the EAAGIGILTV (SEQ ID NO: 71) sequence. (FIG. 7B) Intracellular staining for Melan A with an unconjugated anti-Melan A antibody and PE conjugated secondary antibody confirmed the absence of Melan A protein. (C&D) Activation assays (TAPI-0 with TNF and CD107a antibodies) of TIL MM909.24 (FIG. 7C) and CR24 (FIG. 7D) with wild-type and Melan A knock-out (KO) autologous melanomas. Melan A peptide EAAGIGILTV (SEQ ID NO: 71) was used as a positive control for CR24. CR24 was still capable of recognising autologous melanoma lacking Melan A expression, and therefore HLA A2-EAAGIGILTV (SEQ ID NO: 71) presentation, suggesting that at least one other peptide was being recognised by CR24, and most likely those derived from BST2 and/or IMP2.

Figure 8A:
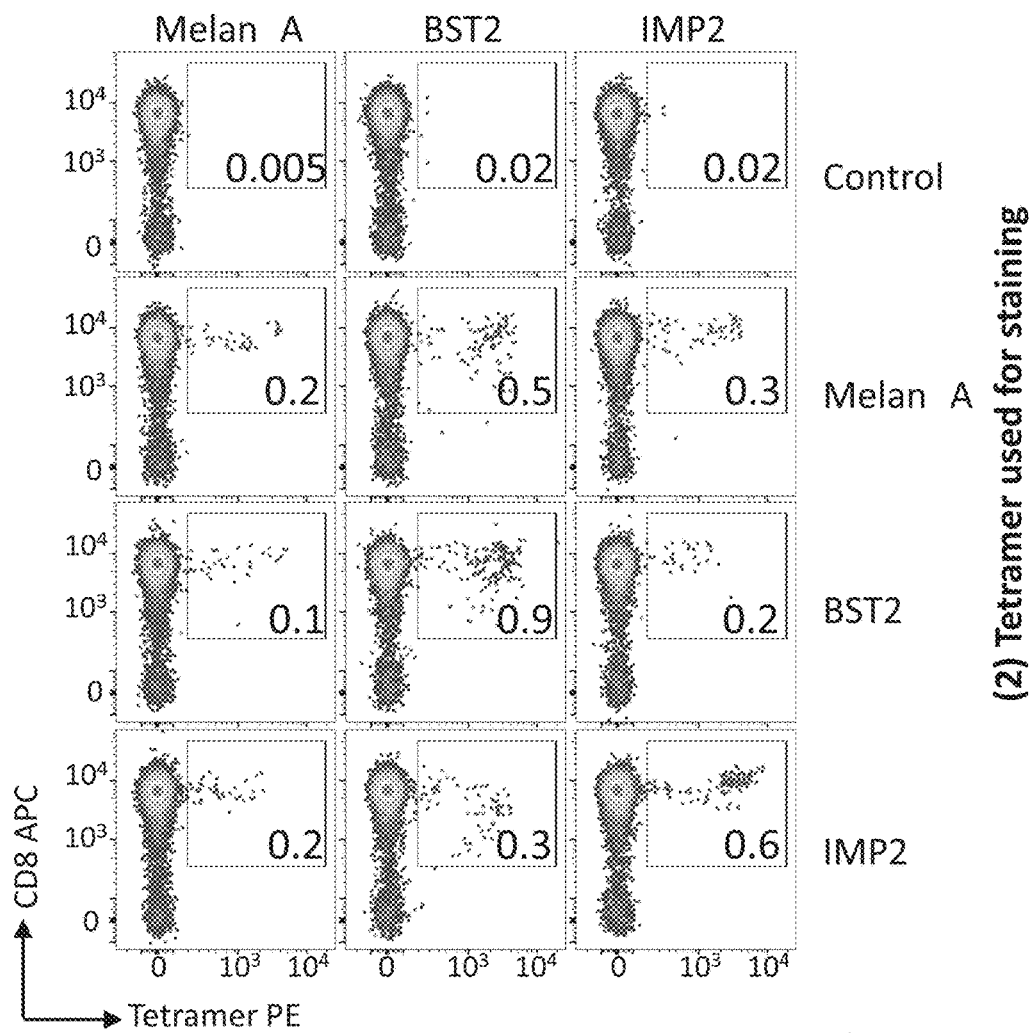
Figure 8B:
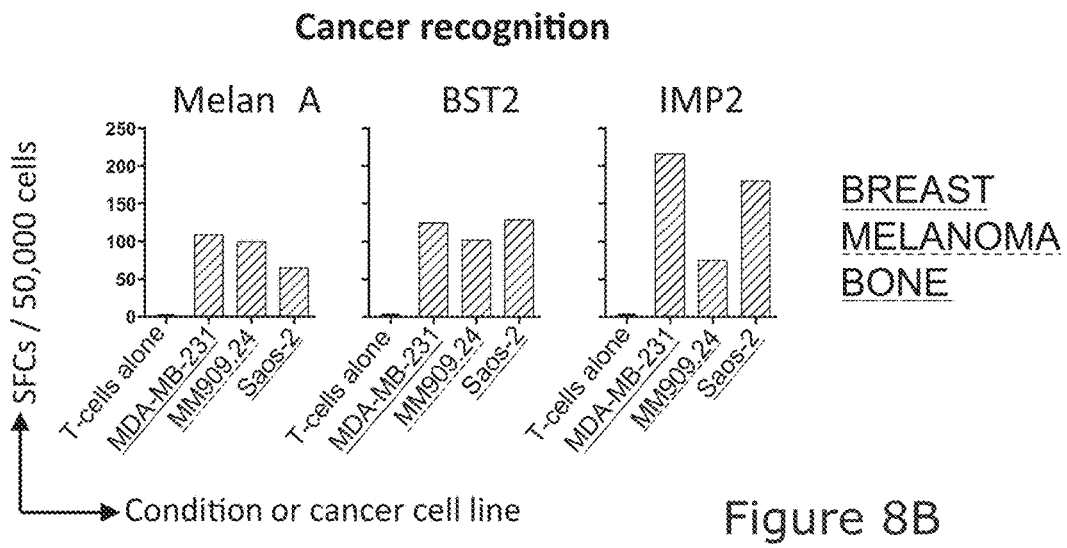

FIGS. 8A-8B show T-cells cross-reactive for Melan A (EAAGIGILTV (SEQ ID NO: 71)), BST2 (LLLGIGILVL (SEQ ID NO: 72)) and IMP2 (NLSALGIFST (SEQ ID NO: 73)) peptides can be generated from healthy donor(s). (FIG.

8A) CD8 T-cells from two HLA A2+ donors (representative data from one donor is shown) were primed as separate cultures with Melan A, BST2 or IMP2 peptide (1). Two weeks post priming each culture was stained with control (ALWGPDPAAA (SEQ ID NO: 86) from preproinsulin 15-24), Melan A, BST2 and IMP2 tetramers (2). The percentage of cells staining is shown for each sample. (FIG. 8B) Each of the primed T-cell lines was used in overnight IFNγ ELISpot assay with the cancer cell lines; MDA-MB-231 (breast), MM909.24 (melanoma) and Saos-2 (bone). T-cells were also incubated alone. The number of spot forming cells (SFCs) per 50,000 cells is shown.

Figure 9A:
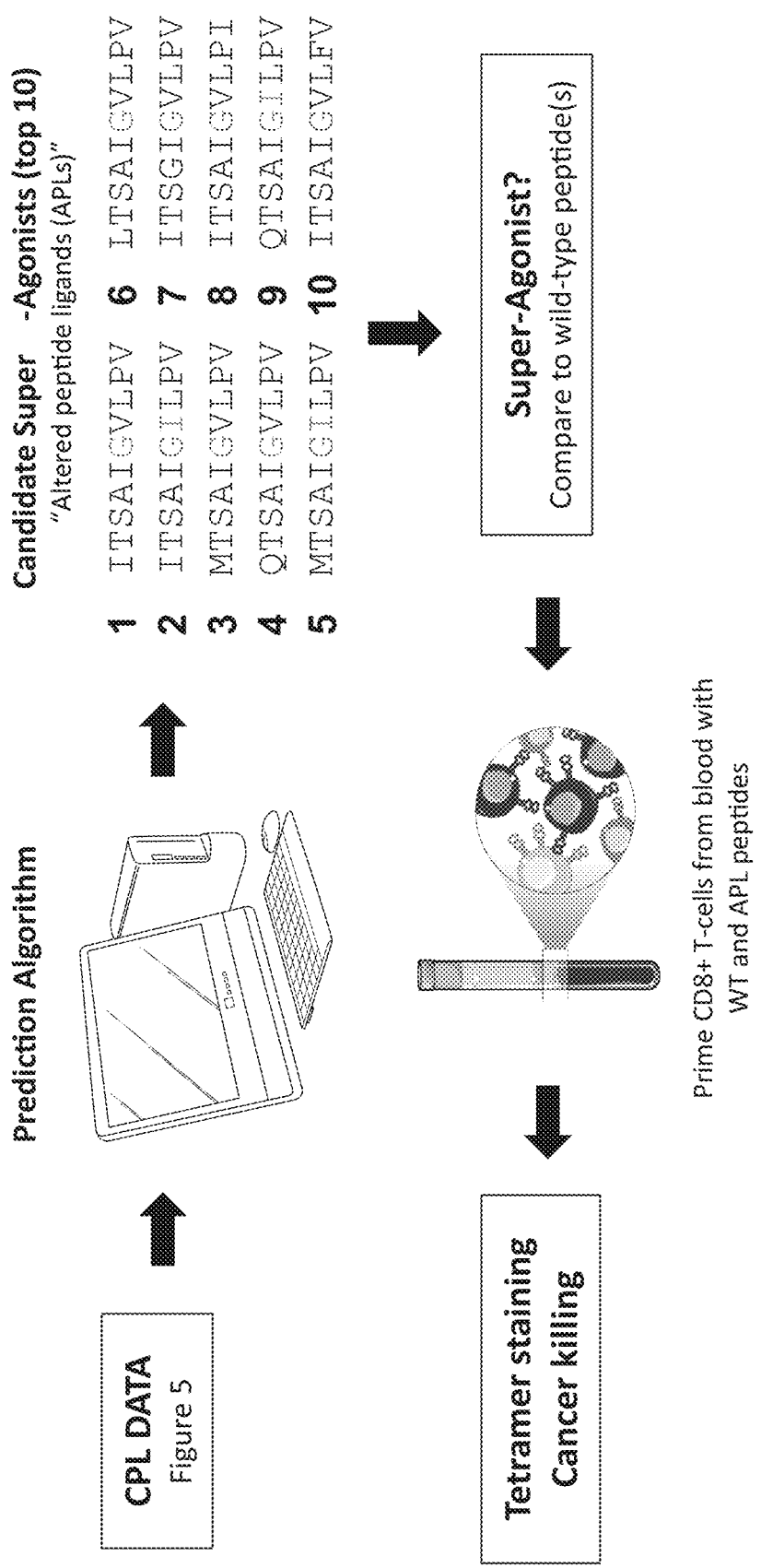
Figure 9B:
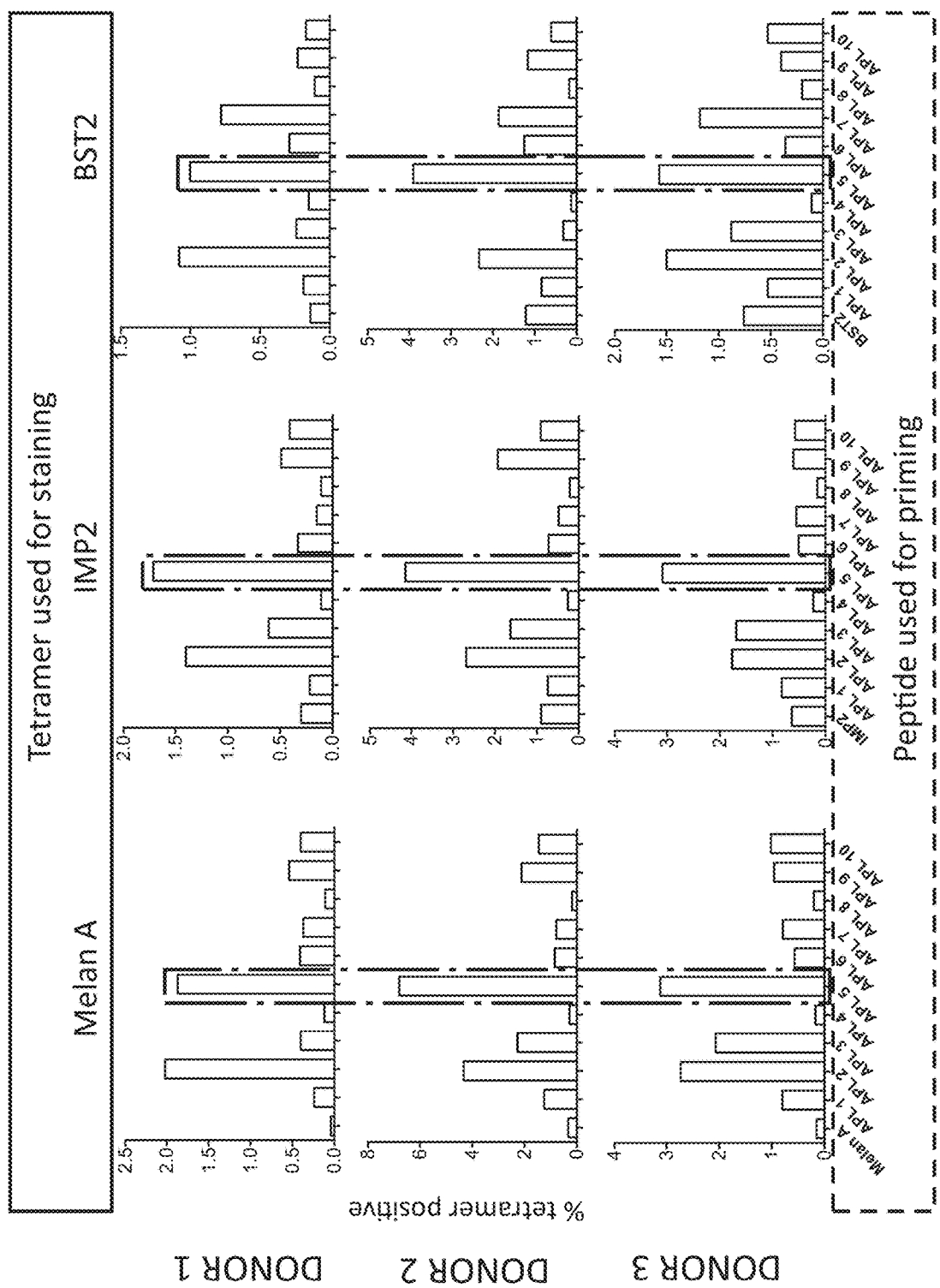

FIGS. 9A-9B show that super-agonist peptide for multipronged T-cells primes more cancer-peptide specific T-cells than the wild-type peptides. Candidate super-agonists were designed using CPL data for CR24 (FIG. 5) and a prediction algorithm (wsbc.warwick.a.uk/wsbcToolsWebpage/user_cases.php); which identifies the peptides most likely to act as a super-agonist based on the amino acid preferences revealed by the CPL data (2: https://www.ncbi.nlm.nih.qov/pubmed/22952231). The peptides are sequence dissimilar to the wild-type peptide and termed altered peptide ligands. The top ten peptides (SEQ ID NOs: 76 to 85) are shown in (FIG. 9A) and share either a Glycine at position 6 (Altered peptide ligands (APL), 1, 3, 4, 6, 7, 8 and 10) or Glycine and Isoleucine at positions 6 and 7 respectively (APL peptides 2, 5 and 9), with wild-type peptides EAAGIGILTV (SEQ ID NO: 71) (Melan A), LLLGIGILVL (SEQ ID NO: 72) (BST2) and NLSALGIFST (SEQ ID NO: 73) (IMP2) (shown in bold). (FIG. 9B) To test the APLs for super-agonist properties each of the WT and APL peptides were used to prime CD8+ T-cells from HLA A2+ healthy donors. The magnitude of the response to each of the peptides was assessed by staining the T-cells with tetramers for HLA A2-EAAGIGILTV (Melan A) (SEQ ID NO: 71), -LLL-GIGILVL (SEQ ID NO: 72) (BST2) or -NLSALGIFST (SEQ ID NO: 73) (IMP2). Overall, APL 5 (MTSAIGILPV) (SEQ ID NO: 80) seemed to be the most effective super-agonist at priming Melan A, BST2 and IMP2 T-cells across all three donors tested, with APL 2 (ITSAIGILPV) (SEQ ID NO: 77) also exhibiting effect across each donor.

Figure 10A:
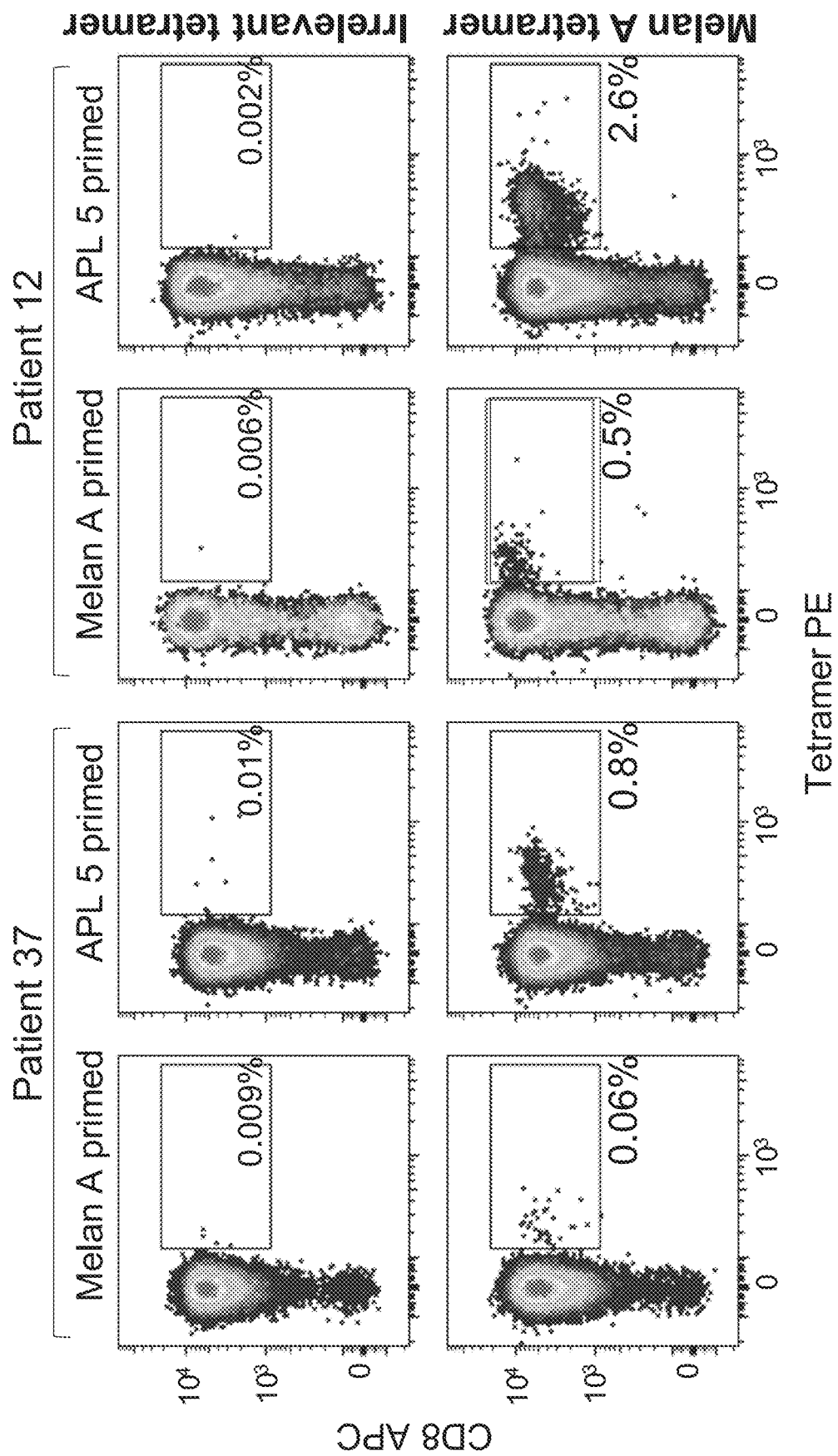
Figures 10B, 10C:
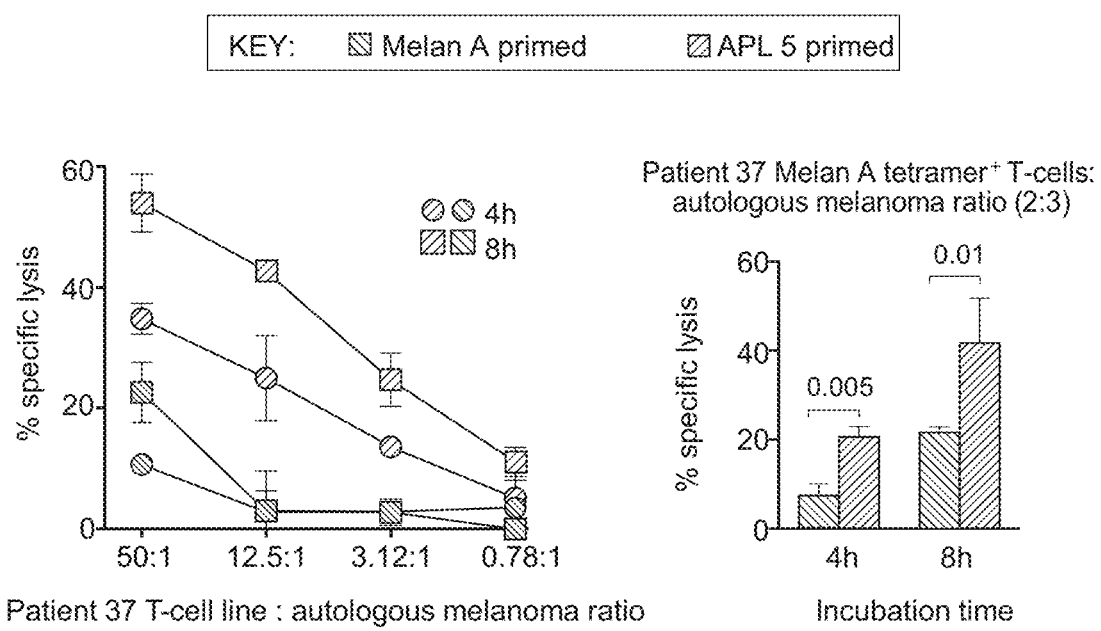

FIGS. 10A-10C show that super-agonist peptide number 5 (MTSAIGILPV) (SEQ ID NO: 80) primed more CD8 T-cells from metastatic melanoma patients able to recognise WT EAAGIGILTV Melan A peptide (SEQ ID NO: 71). Due to the limited number of PBMCs available from patients 37 and 12 only the Melan A peptide was used for comparison to peptide number 5. Patient 37 is now deceased having not responded to conventional or TIL therapy. Patient 12 was undergoing therapy. (FIG. 10A) HLA A2-EAAGIGILTV (WT Melan A) (SEQ ID NO: 71) tetramer staining data following priming of CD8+ T-cells with EAAGIGILTV (WT) (SEQ ID NO: 71) and MTSAIGILPV (SEQ ID NO: 80) (number 5) peptides. Irrelevant HLA A2-ALWGPD-PAAA (preproinsulin) (SEQ ID NO: 86) tetramer used as an irrelevant control. (FIG. 10B) Chromium release cytotoxicity assay performed for the T-cell lines from patient 37 using autologous melanoma. The T-cell line to melanoma cell ratio displayed is based on total T-cell number. Insufficient cells were available from patient 12 to perform the killing assay. (FIG. 10C) Cytotoxicity assay as in B, but with cell numbers adjusted according to EAAGIGILTV (SEQ ID NO: 71) tetramer positivity shown in (FIG. 10A), to give 2 EAA-GIGILTV (SEQ ID NO: 71) tetramer+ cell per 3 melanoma cells, for both the EAAGIGILTV (SEQ ID NO: 71) and MTSAIGILPV (SEQ ID NO: 80) primed T-cell lines. P values are displayed for an unpaired one-tailed t-test.

Figure 11:
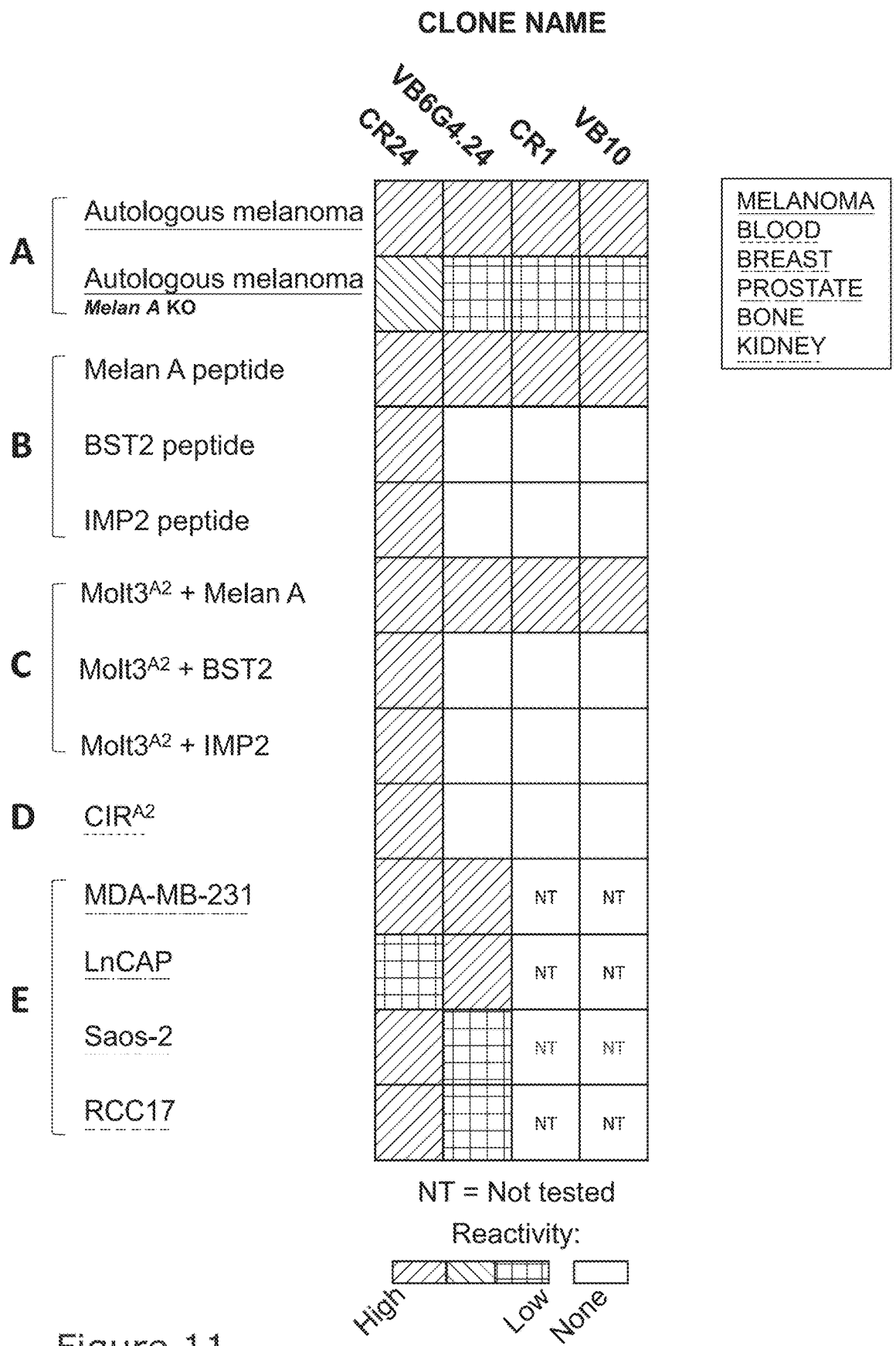

FIG. 11 shows summarised preliminary data from other potentially multipronged T-cells. T-cell clones (VB6G4.24, CR1 and VB10) also grown from TIL patient MM909.24 recognise the Melan A peptide (EAAGIGILTV) (SEQ ID NO: 71) but not BST2 (LLLGIGILVL) (SEQ ID NO: 72) or IMP2 (NLSALGIFST) (SEQ ID NO: 73) peptides (neither as exogenous peptide nor from transduced protein expressed by MOLT3s). The CDR3 sequence of the beta TCR chain from VB6G4.24 appeared in clonotyping data for all ten cancer cell lines in FIGS. 2A-2B, suggesting that this clone responds to multiple cancer cells lines but not by recognition of the IMP2 or BST2 peptides.

Figure 12A:
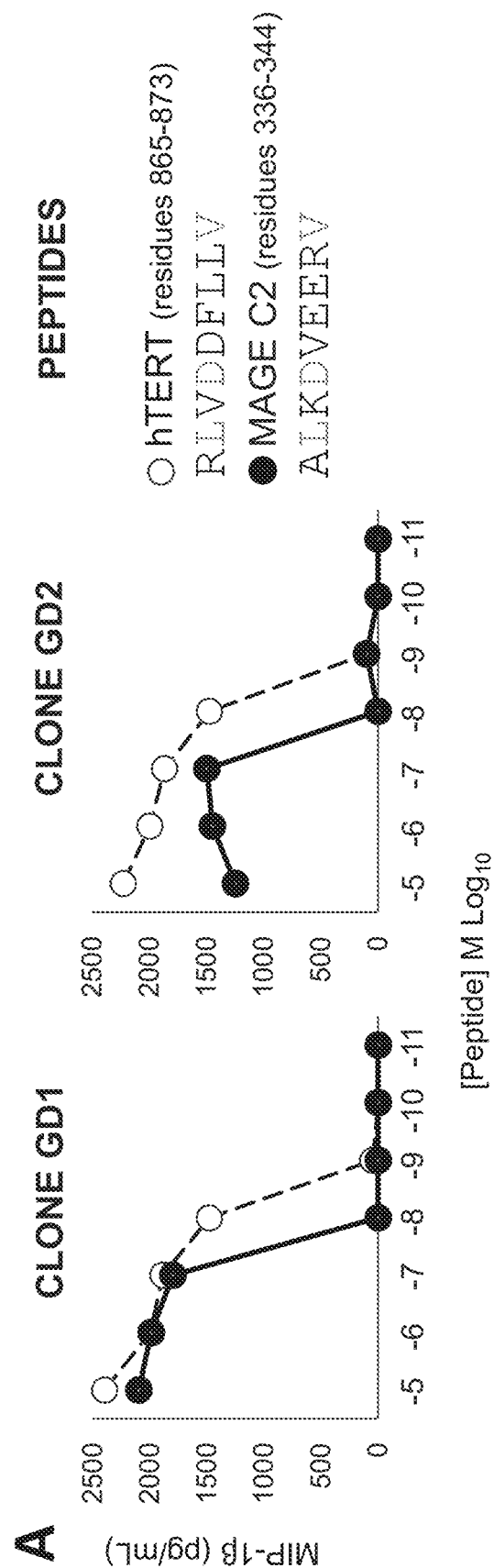
Figure 12C:
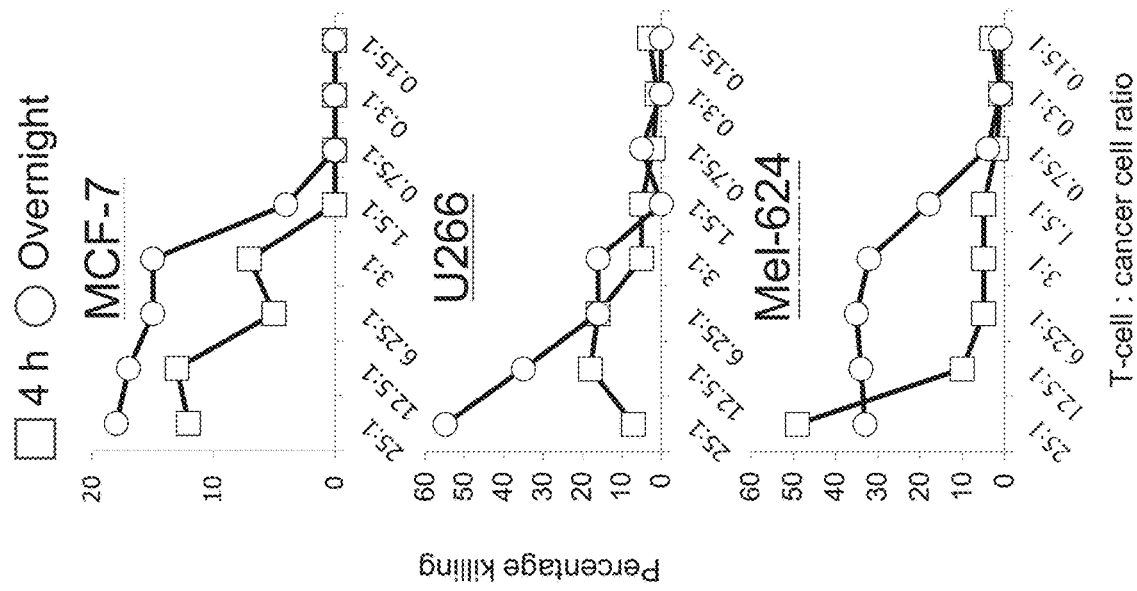
Figure 12B:
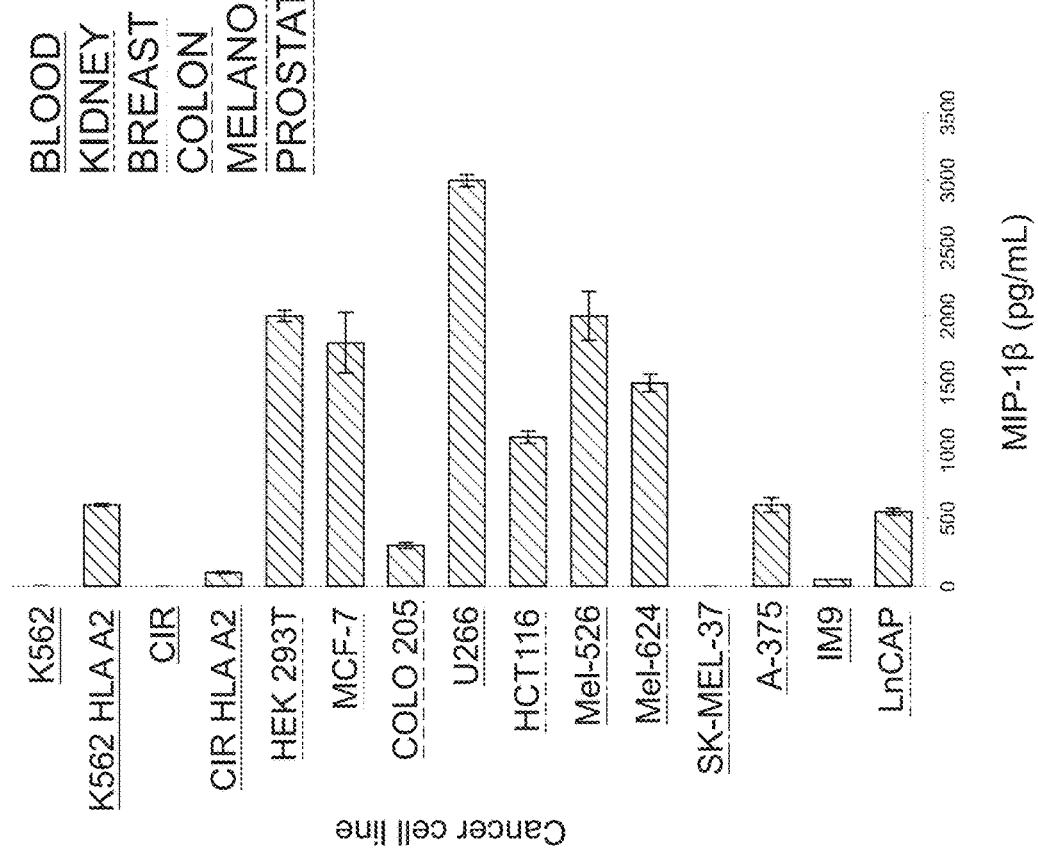

FIGS. 12A-12C show the peptide cross-reactivity of other multipronged T-cells. Clones GD1 and GD2 recognise different peptides than clone CR24. (FIG. 12A) HLA A2-restricted clones GD1 and GD2 grown from different donors express different T-cell receptors but recognise the same peptides from human telomerase reverse transcriptase (hTERT, SEQ ID NO: 74) and MAGE C2 (SEQ ID NO: 75), as shown. Only the red amino acid residues are common to each of the peptides. Overnight activation assay with each of the clones using decreasing concentrations of each of the peptides. Supernatants were harvested and used for MIP-1β ELISA. (FIG. 12B) Preliminary screening of GD1 for recognition of cancer cell lines with different tissue origin. Overnight activation assay and MIP-1β ELISA. (FIG. 12C) Chromium release cytotoxicity assay with cell lines identified in (FIG. 12B) as being good targets of GD1. Percent specific lysis assessed after 4 h and overnight incubation.

FIGS. 13A-13B show multipronged cancer specific T-cells and T-cell receptors differ from normal anti-cancer T-cells. (FIG. 13A) Conventionally, anti-cancer T-cells recognise cancer cells when the TCR binds to a peptide derived from cancer antigens as shown in A. These T-cells do not respond to other cancer-derived peptides. (FIG. 13B) Unusually, multipronged anti-cancer T-cells bear TCRs that recognise multiple different cancer peptides. It is far more difficult for cancer cells and a developing tumour to escape from multipronged T-cells. Consequently, the use of multipronged TCRs is desirable in cancer immunotherapy approaches.

Figure 14A:
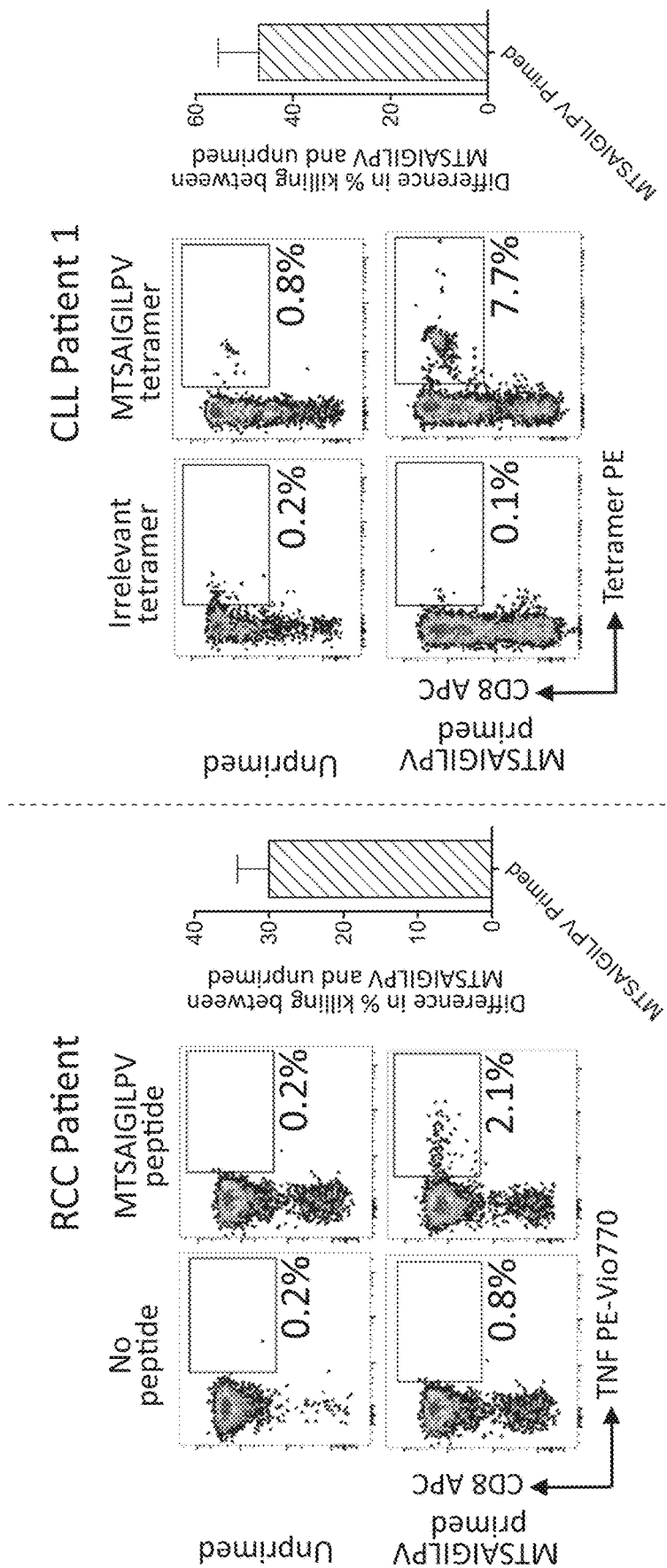
Figure 14:
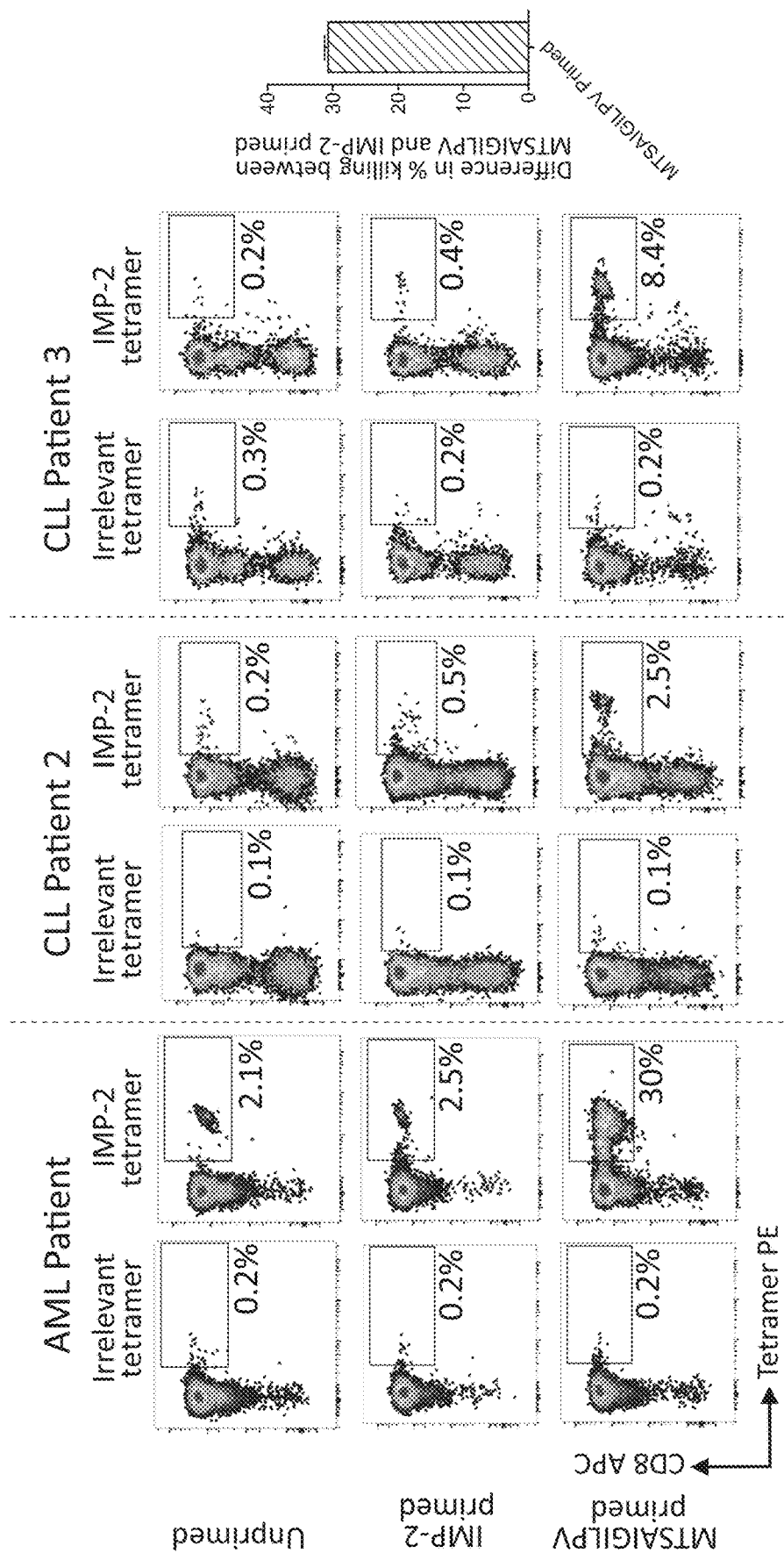

FIGS. 14A-14B show super-agonist peptide MTSAIGILPV (SEQ ID NO: 80) primed a greater proportion of cancer-specific T-cells leading to enhanced killing of autologous cancer. (FIG. 14A) CD8 T-cells from a renal cell carcinoma (RCC) and chronic lymphocytic leukaemia (CLL) patient were left unprimed or primed with MTSAIGILPV (SEQ ID NO: 80) peptide for 28 days. A TAPI-0 assay (RCC patient) or tetramer staining (CLL patient) demonstrated the presence of MTSAIGILPV (SEQ ID NO: 80) specific T-cells. The MTSAIGILPV (SEQ ID NO: 80) primed CD8s killed more autologous cancer cells than the unprimed T-cells. (FIG. 14B) CD8 T-cells from an acute myeloid leukaemia (AML) patient and two CLL patients were left unprimed, or primed with either wild-type IMP-2 (NLSALGIFST) (SEQ ID NO: 73) or MTSAIGILPV (SEQ ID NO: 80) peptide for 28 days. Analysis performed with IMP-2 tetramer revealed that the unprimed and IMP-2 primed conditions had similar proportions of IMP-2 specific T-cells, whereas MTSAIGILPV broke tolerance and induced a greater proportion of IMP-2 cells. T-cells from CLL patient 3 were used in a killing assay and the MTSAIGILPV (SEQ ID NO: 80) primed T-cells killed more CLL cells than the IMP-2 primed CD8s.

FIG. 15 shows a schematic of how the multipronged T-cells recognise a plurality of different peptides derived from the different cancer-specific antigens at the surface of the same cancer cell.

Figure 16:
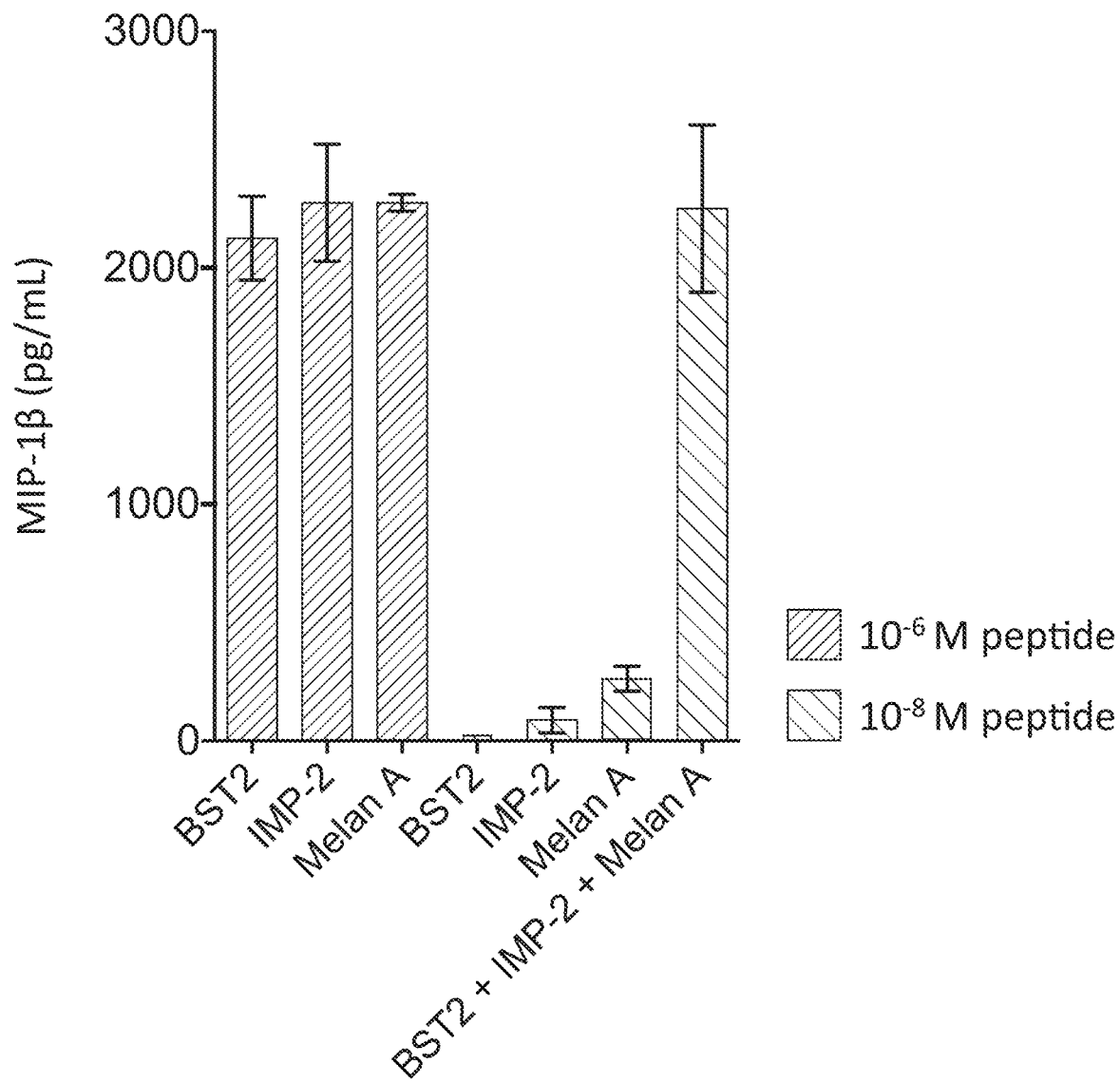

FIG. 16 shows multipronged T-cells recognise peptides additively and at low concentration. Multipronged T-cell clone CR24 recognizes peptides from BST2 (LLL-GIGILVL) (SEQ ID NO: 72), Melan A (EAAGIGILTV) (SEQ ID NO: 71) and IMP2 (NLSALGIFST) (SEQ ID NO: 73). CR24 responded to all three individual peptides at 10-6 M, but responses dropped when peptides were at 10-8 M. However, CR24 exhibited good activation when each peptide was present at 10-8 M within a mix of peptides. This demonstrates how multipronged T-cells can sensitively target cancer cells by recognition of multiple peptides from different proteins expressed by the same cell.

DETAILED DESCRIPTION

Methods and Materials
General Cell Culture Reagents and Cell Lines

RMPI-1640 with 2 mM L-glutamine, 100 U/mL penicillin and 100 µg/mL streptomycin (termed RO) was supplemented with either 5% (R5) or 10% (R10) foetal calf serum. T-cell media was R10 with added 10 mM HEPES buffer, 0.5× non-essential amino acids, 1 mM sodium pyruvate, 20-200 IU/mL of IL-2 (Aldesleukin, Proleukin, Prometheus, San Diego, CA, USA) and 25 ng/mL of IL-15 (Peprotech, Rocky Hill, NJ, USA). D10-F12 media was made as for R10 using DMEM-F12. Unless otherwise stated tissue culture reagents were from Life Technologies (Carlsband, CA, USA). Cell lines C1R, T2 and IM9 were cultured as suspension cells in R10. Malignant melanoma cell lines Mel-526, Mel-624, FM-2, FM-56, SK-MEL-37 and A-375 were cultured as adherent cells in R10. Melanoma MM909.24 and renal cell carcinoma RCC17 were obtained from patients treated at the CCIT and cultured as suspension cells in R10 and D10-F12 respectively. Other cancer cell lines were maintained as described by the ATCC; breast adenocarcinoma MDA-MB-231 (ATCC® HTB-26™) and MCF-7 (ATCC® HTB-22™); prostate adenocarcinoma LnCAP (ATCC® CRL-1740™); colorectal carcinomas COLO 205 (ATCC® CCL-222™) and HCT116 (ATCC® CCL-247™); lung carcinoma H69 (ATCC® HTB-119™); liver hepatocellular carcinoma HepG2 (ATCC® HB-8065™); cervical carcinoma MS751 (ATCC® HTB-34™); acute lymphoblastic leukaemia MOLT3 (ATCC® CRL-1552™); chronic myeloid leukaemia K562 (ATCC® CRL-3344™); myeloma/plasmacytoma U266 (ATCC® TIB-196™) osteosarcomas U-2 OS (ATCC® HTB-96™) Saos-2 (ATCC® HTB-85™) and TK143 (ATCC® CRL-8303™); HEK293T embryonic kidney cell (ATCC® CRL-1573™); acute monocytic leukaemia THP-1 (ATCC® TIB-202™); and kidney carcinoma A-498 (ATCC® HTB-44™).

Melanoma Tumour Infiltrating Lymphocytes Recognise Multiple Cancer Cell Types

Stage IV metastatic melanoma patient MM909.24 underwent rapid tumour infiltrating therapy for at the Centre for Cancer Immunotherapy (CCIT), Herlev Hospital, Copenhagen [1]. To date, this patient has experienced lasting remission. Chromium release cytotoxicity assay was used to assess reactivity towards cancer cell lines: autologous melanoma (MM909.24), MDA-MB-231, MCF-7, LnCAP and RCC17. Cell lines (1×10$^6$ cells) were labelled for 1 h with 30 µCi of sodium chromate (51Cr) (Perkin Elmer, Waltham, MA, USA), leached for 1 h, then cultured with TILs overnight. A 10:1 TIL to target cell (2000 cells per well) ratio was used. After overnight incubation supernatants were harvested, mixed with scintillant and read using a microbeta counter and specific lysis calculated [2]. Further cancer cell lines were tested using a TNF processing inhibitor-0 (TAPI-0) assay [3]; TILs were harvested from culture washed with RO and rested overnight in R5 media. On the day of the activation assay, cells were harvested then counted and 100,000 incubated with 30 µM TAPI-0 (Sigma-Aldrich) anti-TNF-PE-Vio770™ (clone cA2, Miltenyi Biotech) and anti-CD107a-PE (clone H4A3, BD Biosciences) antibodies in wells of a 96 U well plate. Cancer cell lines were added to give a TIL to target cell ratio of 1:2. In addition to the cancer cell lines above the following were also used; COLO 205, H69, HepG2, MS751 and Saos-2. The cells were incubated for 4-5 h at 37° C. then stained at RT for 5 min with 2 µL of LIVE/DEAD fixable dead cell stain ViVid (Life Technologies) that had been diluted 1:40 using PBS. Antibodies to detect surface markers were added directly to each sample without washing; anti-CD8-APC (clone BW135/80, Miltenyi Biotech) and anti-CD3-peridinin chlorophyll (PerCP) (clone BW264/56, Miltenyi Biotech). Data was acquired on a BD FACS Canto II (BD Biosciences) and analysed with FlowJo software (TreeStar Inc., Ashland, OR, USA). Activated TILs (CD107a+ and/or TNF+) were sorted on a BD FACS Aria (BD Biosciences, San Jose, CA, USA) and used for next generation sequencing of the T-cell receptor (TCR) chains as previously described [4].

The Strategy for Identifying Peptides Recognised by Orphan CD8 Clones

T-cell clones of unknown peptide specificity (termed orphan clones) were generated by culturing 0.5 cells/well in of 96 U well plates in T-cell media with 50,000 irradiated (3000-3100 cGy) allogenic peripheral blood mononuclear cells (PBMCs) from three donors and 1-2 µg/mL of phytohaemagglutinin (PHA). PBMCs were separated from blood by standard density gradient centrifugation. If needed, red blood cells were lysed using ammonium chloride solution. Blood was procured as buffy coats' from the Welsh Blood Service (Pontyclun, Wales, UK). All human tissue was obtained and handled in accordance with Cardiff University's guidelines to comply with the UK Human Tissue Act 2004. T-cell clones were screened against autologous melanoma (MM909.24) and in some case cancer cell lines of different tissue origin. Clones of interest were grown to large number in T25 flasks using the PBMC and PHA method as above. Combinatorial peptide library (CPL) and cancer antigen database screening was performed to find peptides recognized by orphan clones. Combinatorial peptide libraries were synthesized and used as previously described [5,6]. Briefly, long-term storage was at −80° C. as 20 mM DMSO stocks with 1 mM working dilutions made in sealable (silicone sealing mat, AxyGen® AxyMat™, Corning, New York, US) 2 mL deep round-well plates (AxyGen®, Corning) with RO (as for R10 but with no serum), which were stored at 4° C., then vortexed (MixMate®, Eppendorf®, Hamburg, Germany) at 1300 rpm for 1 min, then centrifuged (400 g, 5 mins) before use. Each sub-library was used at a concentration of 100 µM with respect to total peptide concentration. The CPL data was run via a database, which contains the amino acid sequences of proteins expressed by cancers (manuscript in preparation). The cancer antigen database will be available online as part of the PI CPL (peptide identification combinatorial peptide library) webtool hosted by Warwick University's Systems Biology Centre (wsbc.warwick.ac.uk/wsbcToolsWebpage/user_cases.php). Candidate peptides from the database were automatically ranked based on their likelihood of being recognised by a clone, with the top 20 being tested in peptide titration assays.

CR24 Recognises Multiple Cancer Cell Types

HLA A2+ Melanomas, MM909.24 (autologous), Mel-526, Mel-624, and HLA A2+ non-melanomas, C1R-HLA A2, MDA-MB-231, Saos-2, U205, A498, TK143, HEK293T, COLO 205, HCT116, HeLa, HepG2 and THP1 were used as target cells in a TAPI-0 assay, which is described above. HLA A2neg melanomas FM-2 and FM-56, and wild-type C1Rs (HLA A2neg) were used as controls.

Combinatorial Peptide Library (CPL) and Cancer Antigen Database Screening of Clone CR24

CR24 was rested overnight in R0 then 30,000 used per well of the decamer CPL screen (details above). The peptide length preference of CR24 had previously been established using sizing scan assays [7] (data not shown). T2 cells (60,000 per well) were used as antigen presenting cells. The assay was performed in R5 and supernatants harvested for MIP-1β enzyme linked immunosorbent assay (ELISA) according to the manufacturer's instructions (R&D Systems, Minneapolis, MN, USA).

CR24 Recognises Three HLA A2 Restricted Peptides from Different Cancer Proteins

CR24 was cultured overnight in R5, then 30,000 used per well of a 96 U well plate with decreasing concentrations of peptides. After overnight incubation supernatants were used MIP-1β ELISA according to the manufacturer's instructions (R&D Systems, Minneapolis, MN, USA). For tetramer analysis CR24 (20,000-50,000 per sample) was stained in 5 mL polypropylene tubes suitable for flow cytometry. Cells were treated in 100 μL of FACS buffer (PBS+2% FBS) with 50 nM Dasatinib (a protein kinase inhibitor) for 30 min at 37° C. and phycoerythrin (PE) conjugated tetramer (0.5 μg) added directly to the sample before being moved to ice for a further 30 min [8]. Tetramer was washed with 3 mL of FACS buffer (700 g, 5 min) then labelled with 0.5 μg (10 μg/mL) of mouse anti-PE unconjugated antibody (clone PE001, BioLegend, London, UK) for a further 20 min on ice [8]. To test if CR24 could recognise endogenously express antigen MOLT3 cells were used to express various proteins. Codon optimised full-length human HLA A2 (IMGT/HLA Acc No: HLA00005), MLANA (Melan A) (UniProtKB Q16655), BST2 (UniProtKB Q10589), IGF2BP2 (IMP2) (UniProtKB Q9Y6M1), COL6A2 (a2 subunit of collagen type VI) (UniProtKB P12110) and Zika virus (Rio-U1) ancC (GenBank KU926309.2) genes were synthesized (Genewiz, South Plainfield, NJ, USA) and cloned into the 3rd generation lentiviral transfer vector pELNS (kindly provided by Dr. James Riley, University of Pennsylvania, PA, USA). The pELNS vector contains a rat CD2 (rCD2) marker gene separated from the gene of interest by a self-cleaving 2A sequence. Lentiviral particle production, calcium chloride transfection and rCD2-based purification of cells were performed as previously described [9].

Clone CR24 is Able to Recognise Autologous Melanoma Lacking Melan A Expression

To demonstrate that CR24 can target autologous melanoma through multiple antigens, guide RNAs to ablate Melan A expression using CRISPR/Cas9 were designed using the cripsr.mit.edu webtool, applied and the Melan A gene sequenced to confirm disruption (data not shown). Intracellular staining for Melan A was performed using Cytofix/Cytoperm™ reagents according to manufacturer's instructions (BD Biosciences). A primary unconjugated rabbit anti-Melan A antibody (clone EP1422Y) (Abcam, Cambridge, UK) was used with a secondary PE conjugated goat anti-rabbit antibody. Wild type and Melan A KO MM909.24 melanomas were used TAPI-0 assays, as described above, with both TILs and CR24.

T-Cells that Recognise the Same Three Peptides as CR24 are Present in Healthy HLA A2+ Donors To generate T-cell peptide lines, CD8 T-cells were purified from the PBMCs of HLA A2+ donors using CD8 microbeads according to the manufacturer's instructions (Miltenyi Biotech, Bergisch Gladbach, Germany). Purified CD8 cells ($3\times10^6$) were co-incubated with autologous CD8neg cells ($6-8\times10^6$) in 24 well plates in 2 mL of T-cell media, but with no IL-15. 25 μM of each peptide was used. The cultures had 50% of the media changed thrice weekly. Tetramer staining was performed as above, using 500,000 cells per tube. Each T-cell line was used in an IFNγ enzyme linked immunosorbent spot (ELISpot) assay with cell lines MDA-MB-231, melanoma MM909.24 and Saos-2. 50,000 T-cells and 15,000 cancer cells were used per well. Incubation was performed for 48 h, and the assay developed according the manufacturer's instructions (Mabtech, Nacka Strand, Sweden).

Super-Agonist Peptides Prime Multi-Pronged T-Cells for Improved Cancer Cell Recognition.

CPL assay of CR24 was performed as described above. Candidate peptide agonists were designed using the CR24 CPL and an online algorithm (wsb.warwick.ac.uk/wsbc-ToolsWebpage/user_cases.php). Priming of CD8 T-cells from healthy donors, tetramer staining and chromium release cytotoxicity assays were performed as described above.

Other Melan A Clones do not Recognise the BST2 and IMP2 Peptides Seen by CR24

TAPI-0 and activation assays (ELISA) were performed for VB6G4.24, CR1 and VB10, as described above for CR24. The data was summarised in tabular from.

Clone Recognition of Peptides from Cancer Antigens hTERT and MAGE C2

Clones GD1 and GD2 were grown from the peripheral blood of different HLA A2+ healthy donors. The clones were used in overnight activation assays with decreasing concentrations of respective peptides, and supernatants used for MIP-1β ELISA, as described above. An overnight activation was performed with GD1 and target cells; K562, K562 HLA A2, C1R, C1R HLA A2, HEK 293T, MCF-7, COLO 205, U266, HCT116, Mel-526, Mel-624, SK-MEL-37, A375, IM9 and LnCAP. Supernatants were harvested and used for MIP-1β ELISA. A chromium release cytotoxicity assay was performed, as above, with cell lines MCF-7, U266 and Mel-624. Incubation times of 4 h and overnight, with varying T-cell to target cell ratios were used.

Results

1. Tumour infiltrating lymphocytes (TILs) derived from a metastatic melanoma patient that underwent successful immunotherapy are capable of killing and recognising autologous melanoma and HLA A2+ cancer cell lines originating from a range of cancers: breast, colon, lung, liver, prostate, cervix, bone and kidney (FIGS. 1A-1C).

2. T-cell receptor clonotyping of cancer reactive TILs revealed that the same T-cells recognised multiple HLA A2+ cancer cell lines (FIGS. 2A-2B). 50% of the T-cells (TCRs) recognised more than 4 cancer cell lines and, 8.6% (5 TCRs) recognised all 10 cell lines tested. Further experiments aimed at understanding the pan cancer cell line recognition resulted in the discovery that a single T-cell can recognise multiple peptides originating from different cancer proteins.

3. In order to map the peptide specificities of the T-cells from the TILs, the T-cells were firstly cloned, then screened for reactivity towards various cancer cell lines. Clone CR24 exhibited reactivity towards autologous melanoma and cancer cell lines from breast, bone, kidney, blood, colon, cervix and liver (FIGS. 4A-4C). This reactivity was mediated through HLA A2 as HLAA2neg melanomas and wildtype CIR cells (HLAA2neg) were not recognised.

4. Combinatorial peptide library and cancer antigen database screening (as described in FIGS. 3A-3D) of CR24 (FIG. 5) revealed multiple peptides that were predicted to be seen by CR24 (data not shown), with three of them being recognised when tested as exogenous peptide (FIGS. 6A-6C). CR24 also stained with HLA A2 tetramers containing the three peptides (FIG. 6A-6C). The peptides; EAAGIGILTV (SEQ ID NO: 71) from Melan A (residues 26-35), LLLGIGILVL (SEQ ID NO: 72) from BST2 (residues 22-31) and NLSALGIFST (SEQ ID NO: 73) from IMP2 (residues 367-376). These data demonstrate that CR24 is cross-reactive for distinct peptides derived from different cancer proteins.

5. The peptides recognised by CR24 are processed and presented from endogenously expressed proteins, as CR24 was capable of recognising antigen presenting cells (MOLT3) made to stably express either Melan A, BST2 or IMP2 (FIGS. 6A-6C).

6. It would be extremely difficult for cancer cells to escape from T-cells that were targeting them through more than one different cancer antigen as escape would require simultaneous mutation of all targets that lowered or ablated presentation of all cognate peptides. To demonstrate this, we targeted autologous melanoma (MM909.24) for ablation of the Melan A gene, which was confirmed by antibody staining to lack Melan A protein expression (Melan A knockout (KO)) (FIGS. 7A-7D). Both the TIL from patient MM909.24 and clone CR24 recognised the Melan A knockout melanomas (FIGS. 7A-7D). For CR24, reactivity against wild type autologous tumour was 71% and for the Melan A KO 55%. It is highly likely that CR24 was recognising the Melan A KO melanoma through the BST2 and/or IMP2 peptides and therefore able to mediate destruction of the melanoma.

7. CD8 T-cells able to recognise the Melan A, BST2 and IMP2 peptides seen by CR24 can be generated from the peripheral blood of healthy HLA A2+ donors (FIGS. 8A-8B).

8. Super-agonists designed for multi-pronged T-cells primed a greater proportion of CD8 T-cells capable of recognising WT Melan A (EAAGIGILTV) (SEQ ID NO: 71), BST2 (LLLGIGILVL) (SEQ ID NO: 72) and IMP2 (NLSALGIFST) (SEQ ID NO: 73) peptides, compared to parallel priming with the WT peptides. Super-agonist MTSAIGVLVP (SEQ ID NO; 80) (peptide 5) seemed to be the most effective of the candidate super-agonists at priming (FIG. 9B), eliciting Melan A, BST2 and IMP2 reactive T-cells in all donors tested (n=3). Additionally, MTSAIGILPV (SEQ ID NO; 80) and ITSAIGILPV (SEQ ID NO; 77) were superior at priming Melan A (EAAGIGILTV) T-cells from metastatic melanoma patients compared to the WT EAAGIGILTV peptide (FIG. 10A), and MTSAIGILPV (SEQ ID NO; 80) also in renal cell carcinoma (RCC) and chronic lymphocytic leukaemia (CLL) patients (FIG. 14A) and acute myeloid leukaemia (AML) patients (FIG. 14B). Importantly, the MTSAIGILPV (SEQ ID NO; 80) super-agonist peptide primed T-cells exhibited superior lysis of autologous melanoma cells than the WT Melan A peptide primed T-cells (FIGS. 10B and 10C).

9. Clones (GD1 and GD2) grown from the peripheral blood of two healthy HLA A2+ donors cross-react with different peptides than those recognised by CR24. These peptides are derived from different proteins to those recognised by the CR24 T-cell clone; RLVDDFLLV (SEQ ID NO: 74) from human telomerase reverse transcriptase (hTERT) (residues 855-873) and ALKDVEERV (SEQ ID NO: 75) from melanoma associated antigen C2 (MAGE C2) (residues 336-344). GD1 killed breast, blood and melanoma cancer cell lines (FIGS. 9A-9B).

CONCLUSION

The current consensus view is that cancer-specific T-cells recognise cancer cells via a single peptide antigen presented as a peptide at the cell surface in association with HLA (FIG. 10A). We have discovered that some, rare T-cells are able to recognise cancer cells through multiple peptide epitopes that differ in sequence by two or more amino acids and are derived from different cancer antigens (FIG. 10B). Cancer escape from this type of multipronged T-cell is likely to be extremely difficult.

REFERENCES

[1] Andersen R, Donia M, Ellebaek E, Borch T H, Kongsted P, Iversen T Z, et al. Long-Lasting complete responses in patients with metastatic melanoma after adoptive cell therapy with tumor-infiltrating lymphocytes and an attenuated il2 regimen. Clin Cancer Res 2016; 22:3734-45. doi:10.1158/1078-0432.CCR-15-1879.

[2] Ekeruche-Makinde J, Clement M, Cole D K, Edwards E S J, Ladell K, Miles J J, et al. T-cell receptor-optimized peptide skewing of the T-cell repertoire can enhance antigen targeting. J Biol Chem 2012; 287:37269-81. doi: 10.1074/jbc.M112.386409.

[3] Haney D, Quigley M F, Asher T E, Ambrozak D R, Gostick E, Price D A, et al. Isolation of viable antigen-specific CD8+ T cells based on membrane-bound tumor necrosis factor (TNF)-alpha expression. J Immunol Methods 2011; 369:33-41. doi: 10.1016/j.jim 0.2011.04.003.1solation.

[4] Donia M, Kjeldsen J W, Andersen R, Westergaard M C W, Bianchi V, Legut M, et al. PD-1+ polyfunctional T cells dominate the periphery after tumor-infiltrating lymphocyte therapy for cancer. Clin Cancer Res 2017:clincanres.1692.2016. doi:10.1158/1078-0432.CCR-16-1692.

[5] Wooldridge L, Ekeruche-Makinde J, Van Den Berg H A, Skowera A, Miles J J, Tan M P, et al. A single autoimmune T cell receptor recognizes more than a million different peptides. J Biol Chem 2012; 287:1168-77.

[6] Szomolay B, Liu J, Brown P E, Miles J J, Clement M, Llewellyn-Lacey S, et al. Identification of human viral protein-derived ligands recognized by individual MHCI-restricted T-cell receptors. Immunol Cell Biol 2016; 94:573-82. doi:10.1038/icb.2016.12.

[7] Ekeruche-Makinde J, Miles J J, van den Berg H A, Skowera A, Cole D K, Dolton G, et al. Peptide length determines the outcome of TCR/peptide-MHCI engagement. Blood 2013; 121:1112-23. doi:10.1182/blood-2012-06-437202.

[8] Tungatt K, Bianchi V, Crowther M D, Powell W E, Schauenburg A J, Trimby A, et al. Antibody stabilization of peptide-MHC multimers reveals functional T cells bearing extremely low-affinity TCRs. J Immunol 2015; 194:463-74.

[9] Legut M, Dolton G, Mian A A, Ottmann O, Sewell A. CRISPR-mediated TCR replacement generates superior anticancer transgenic T-cells. Blood 2017:blood-2017-05-787598. doi:10.1182/blood-2017-05-787598.

[10] Hundemer M, Schmidt S, Condomines M, Lupu A, Hose D, Moos M, et al. Identification of a new HLA-A2-restricted T-cell epitope within HM1.24 as immunotherapy target for multiple myeloma. Exp Hematol 2006; 34:486-96. doi:10.1016/j.exphem.2006.01.008.

The invention claimed is:

1. A peptide comprising the amino acid sequence of SEQ ID NO: 80, SEQ ID NO: 77, SEQ ID NO: 76, SEQ ID NO: 78, SEQ ID NO: 81, SEQ ID NO: 82, SEQ ID NO: 84, or SEQ ID NO: 85.

2. The peptide of claim 1 comprising the amino acid sequence of SEQ ID NO: 80.

3. The peptide of claim 1, wherein the amino acid sequence of the peptide consists of the amino acid sequence of SEQ ID NO: 80, SEQ ID NO: 77, SEQ ID NO: 76, SEQ ID NO: 78, SEQ ID NO: 81, SEQ ID NO: 82, SEQ ID NO: 84, or SEQ ID NO: 85.

4. The peptide of claim 3, wherein the amino acid sequence of the peptide consists of the amino acid sequence of SEQ ID NO: 80.

5. The peptide of claim 1, wherein the peptide is presented by a human leukocyte antigen class I A (HLA-A) molecule, optionally, wherein the HLA-A molecule is HLA-A2, HLA-A24, HLA-A1, or HLA-A3.

6. A pharmaceutical composition comprising the peptide of claim 1.

7. A vaccine comprising the peptide of claim 1.

8. An immunogenic agent comprising the peptide of claim 1.

9. A combination therapeutic comprising the peptide of claim 1, and a further therapeutic agent.

10. A method of treating cancer in a subject in need thereof, the method comprising administering to the subject the peptide of claim 1.

11. The method of claim 10, wherein the cancer is nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia, T-cell/lymphoma, blood cancer, tonsil, spleen cancer, neuroma, von Hippel-Lindau disease, Zollinger-Ellison syndrome, adrenal cancer, anal cancer, bile duct cancer, bladder cancer, ureter cancer, glioma, oligodendroglioma, neuroblastoma, meningioma, spinal cord tumour, bone cancer, osteochondroma, chondrosarcoma, Ewing's sarcoma, cancer of unknown primary site, carcinoid, carcinoid of gastrointestinal tract, fibrosarcoma, breast cancer, muscle cancer, Paget's disease, cervical cancer, rectal cancer, esophagus cancer, gall bladder cancer, cholangioma cancer, head cancer, eye cancer, nasopharynx cancer, neck cancer, kidney cancer, Wilms' tumor, liver cancer, Kaposi's sarcoma, prostate cancer, testicular cancer, Hodgkin's disease, non-Hodgkin's lymphoma, skin cancer, mesothelioma, myeloma, multiple myeloma, ovarian cancer, endocrine cancer, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer, or tonsil cancer.

12. A method of treating cancer in a subject in need thereof, the method comprising administering to the subject the peptide of claim 3.

13. The method of claim 12, wherein the cancer is nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia, T-cell/lymphoma, blood cancer, tonsil, spleen cancer, neuroma, von Hippel-Lindau disease, Zollinger-Ellison syndrome, adrenal cancer, anal cancer, bile duct cancer, bladder cancer, ureter cancer, glioma, oligodendroglioma, neuroblastoma, meningioma, spinal cord tumour, bone cancer, osteochondroma, chondrosarcoma, Ewing's sarcoma, cancer of unknown primary site, carcinoid, carcinoid of gastrointestinal tract, fibrosarcoma, breast cancer, muscle cancer, Paget's disease, cervical cancer, rectal cancer, esophagus cancer, gall bladder cancer, cholangioma cancer, head cancer, eye cancer, nasopharynx cancer, neck cancer, kidney cancer, Wilms' tumor, liver cancer, Kaposi's sarcoma, prostate cancer, testicular cancer, Hodgkin's disease, non-Hodgkin's lymphoma, skin cancer, mesothelioma, myeloma, multiple myeloma, ovarian cancer, endocrine cancer, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer, or tonsil cancer.

14. A method of treating cancer in a subject in need thereof, the method comprising administering to the subject the peptide of claim 4.

15. The peptide of claim 1 comprising the amino acid sequence of SEQ ID NO: 77.

16. A vector encoding the peptide of claim 1.

17. A method of treating cancer in a subject in need thereof, the method comprising administering to the subject the vector of claim 16.

18. A vector encoding the peptide of claim 3.

19. A method of treating cancer in a subject in need thereof, the method comprising administering to the subject the vector of claim 18.

* * * * *

SEQUENCE LISTING

<160> NUMBER OF SEQ ID NOS: 88

<210> SEQ ID NO 1
<211> LENGTH: 17
<212> TYPE: PRT
<213> ORGANISM: Homo sapiens

<400> SEQUENCE: 1

Cys Ala Thr Ser Asp Arg Gly Gln Gly Ala Asn Trp Asp Glu Gln Phe
1               5                   10                  15

Phe

<210> SEQ ID NO 2
<211> LENGTH: 13
<212> TYPE: PRT
<213> ORGANISM: Homo sapiens

<400> SEQUENCE: 2

Cys Ala Ser Thr Leu Gly Gly Gly Thr Glu Ala Phe Phe
1               5                   10

<210> SEQ ID NO 3
<211> LENGTH: 15
<212> TYPE: PRT
<213> ORGANISM: Homo sapiens

<400> SEQUENCE: 3

Cys Ser Ala Arg Asp Leu Leu Ala Glu Thr Tyr Glu Gln Tyr Phe
1               5                   10                  15

<210> SEQ ID NO 4
<211> LENGTH: 13
<212> TYPE: PRT
<213> ORGANISM: Homo sapiens

<400> SEQUENCE: 4

Cys Ala Ser Ser Ser Ser Asp Thr Asp Thr Gln Tyr Phe
1               5                   10

<210> SEQ ID NO 5
<211> LENGTH: 18
<212> TYPE: PRT
<213> ORGANISM: Homo sapiens

<400> SEQUENCE: 5

Cys Ser Val Glu Gly Ser Leu Gly Arg Ala Leu Arg Ala Asn Glu Gln
1               5                   10                  15

Phe Phe

<210> SEQ ID NO 6
<211> LENGTH: 11
<212> TYPE: PRT
<213> ORGANISM: Homo sapiens

<400> SEQUENCE: 6

Cys Ala Thr His Gly Gly Glu Lys Leu Phe Phe
1               5                   10

<210> SEQ ID NO 7
<211> LENGTH: 14
<212> TYPE: PRT
<213> ORGANISM: Homo sapiens

<400> SEQUENCE: 7

Cys Ala Ser Ser Tyr Val Gly Leu Gly Ser Pro Leu His Phe
1               5                   10

<210> SEQ ID NO 8
<211> LENGTH: 11
<212> TYPE: PRT
<213> ORGANISM: Homo sapiens

<400> SEQUENCE: 8

Cys Ser Gly Gln Ala Asn Thr Glu Ala Phe Phe
1               5                   10

<210> SEQ ID NO 9
<211> LENGTH: 17
<212> TYPE: PRT
<213> ORGANISM: Homo sapiens

<400> SEQUENCE: 9

Cys Ala Ser Ser Pro Thr Thr Gly Leu Lys Thr Arg Ser Gly Tyr Thr
1               5                   10                  15

Phe

<210> SEQ ID NO 10
<211> LENGTH: 12
<212> TYPE: PRT
<213> ORGANISM: Homo sapiens

<400> SEQUENCE: 10

Cys Ser Glu Gly Ser Pro Tyr Asn Glu Gln Phe Phe
1               5                   10

<210> SEQ ID NO 11
<211> LENGTH: 14
<212> TYPE: PRT
<213> ORGANISM: Homo sapiens

<400> SEQUENCE: 11

Cys Ala Ser Ser Asn Gly Phe His Phe Asn Thr Leu Tyr Phe
1               5                   10

<210> SEQ ID NO 12
<211> LENGTH: 13
<212> TYPE: PRT
<213> ORGANISM: Homo sapiens

<400> SEQUENCE: 12

Cys Ala Ser Ser Leu Gly Gly Gly Asp Thr Gln Tyr Phe
1               5                   10

<210> SEQ ID NO 13
<211> LENGTH: 13
<212> TYPE: PRT
<213> ORGANISM: Homo sapiens

<400> SEQUENCE: 13

Cys Ala Ser Ser Phe Ala Gly Thr Asp Thr Gln Tyr Phe
1               5                   10

<210> SEQ ID NO 14
<211> LENGTH: 15
<212> TYPE: PRT
<213> ORGANISM: Homo sapiens

<400> SEQUENCE: 14

Cys Ala Ser Ser Leu Gly Glu Gly Ser Pro Gly Glu Leu Phe Phe
1               5                   10                  15

<210> SEQ ID NO 15
<211> LENGTH: 15
<212> TYPE: PRT
<213> ORGANISM: Homo sapiens

<400> SEQUENCE: 15

Cys Ala Ser Ser Gln Glu Pro Asn Trp Asn Thr Glu Ala Phe Phe
1               5                   10                  15

<210> SEQ ID NO 16
<211> LENGTH: 14
<212> TYPE: PRT
<213> ORGANISM: Homo sapiens

<400> SEQUENCE: 16

Cys Ala Ser Ser Phe Gln Gly Pro Gly Tyr Gly Tyr Thr Phe
1               5                   10

<210> SEQ ID NO 17
<211> LENGTH: 14
<212> TYPE: PRT
<213> ORGANISM: Homo sapiens

<400> SEQUENCE: 17

Cys Ser Ala Arg Asp Thr Thr Trp Gly Leu Glu Gln Tyr Phe
1               5                   10

<210> SEQ ID NO 18
<211> LENGTH: 14
<212> TYPE: PRT
<213> ORGANISM: Homo sapiens

<400> SEQUENCE: 18

Cys Ala Thr Lys Pro Ser Gly Ser Thr Asp Thr Gln Tyr Phe
1               5                   10

<210> SEQ ID NO 19
<211> LENGTH: 14
<212> TYPE: PRT
<213> ORGANISM: Homo sapiens

<400> SEQUENCE: 19

Cys Ser Ala Arg Asp Glu Gly Ile Gly Tyr Glu Gln Tyr Phe
1               5                   10

<210> SEQ ID NO 20
<211> LENGTH: 12
<212> TYPE: PRT
<213> ORGANISM: Homo sapiens

<400> SEQUENCE: 20

Cys Ala Ser Ser Ser Gly Pro Gly Glu Leu Phe Phe
1               5                   10

<210> SEQ ID NO 21
<211> LENGTH: 20
<212> TYPE: PRT
<213> ORGANISM: Homo sapiens

<400> SEQUENCE: 21

Cys Ala Arg Arg Thr Leu Val Ile Val Arg Arg Phe Tyr Ser Gly Asn

-continued

```
1               5                   10                  15

Thr Ile Tyr Phe
            20

<210> SEQ ID NO 22
<211> LENGTH: 16
<212> TYPE: PRT
<213> ORGANISM: Homo sapiens

<400> SEQUENCE: 22

Cys Ser Ala Arg Asp Leu Ile Gly Ser Gln Thr Tyr Glu Gln Tyr Phe
1               5                   10                  15

<210> SEQ ID NO 23
<211> LENGTH: 16
<212> TYPE: PRT
<213> ORGANISM: Homo sapiens

<400> SEQUENCE: 23

Cys Ser Ala Arg Asp Pro Ile Gly Thr Glu Ser Tyr Glu Gln Tyr Phe
1               5                   10                  15

<210> SEQ ID NO 24
<211> LENGTH: 14
<212> TYPE: PRT
<213> ORGANISM: Homo sapiens

<400> SEQUENCE: 24

Cys Ser Ala Arg Asp Arg Ala Gly Arg Ser Pro Leu His Phe
1               5                   10

<210> SEQ ID NO 25
<211> LENGTH: 14
<212> TYPE: PRT
<213> ORGANISM: Homo sapiens

<400> SEQUENCE: 25

Cys Ser Val Glu Glu Ser Ser Gly Ile Tyr Glu Gln Tyr Phe
1               5                   10

<210> SEQ ID NO 26
<211> LENGTH: 15
<212> TYPE: PRT
<213> ORGANISM: Homo sapiens

<400> SEQUENCE: 26

Cys Ser Ala Arg Glu Asp Gly Gly Gln Thr Tyr Glu Gln Tyr Phe
1               5                   10                  15

<210> SEQ ID NO 27
<211> LENGTH: 13
<212> TYPE: PRT
<213> ORGANISM: Homo sapiens

<400> SEQUENCE: 27

Cys Ala Ser Ser Trp Ala Gly Pro Val Glu Gln Tyr Phe
1               5                   10

<210> SEQ ID NO 28
<211> LENGTH: 13
<212> TYPE: PRT
<213> ORGANISM: Homo sapiens

<400> SEQUENCE: 28
```

Cys Ala Ser Ser Ser Gln Gly Arg Ala Glu Gln Tyr Phe
1               5                   10

<210> SEQ ID NO 29
<211> LENGTH: 14
<212> TYPE: PRT
<213> ORGANISM: Homo sapiens

<400> SEQUENCE: 29

Cys Ala Ser Ser Arg Asp Ser Leu Tyr Glu Gln Tyr Phe
1               5                   10

<210> SEQ ID NO 30
<211> LENGTH: 15
<212> TYPE: PRT
<213> ORGANISM: Homo sapiens

<400> SEQUENCE: 30

Cys Ala Ser Ser Leu Gly Ile Ile Ser Gly Gln Pro Gln His Phe
1               5                   10                  15

<210> SEQ ID NO 31
<211> LENGTH: 13
<212> TYPE: PRT
<213> ORGANISM: Homo sapiens

<400> SEQUENCE: 31

Cys Ala Ser Ser Asn Thr Gly Gly Tyr Thr Gln Tyr Phe
1               5                   10

<210> SEQ ID NO 32
<211> LENGTH: 15
<212> TYPE: PRT
<213> ORGANISM: Homo sapiens

<400> SEQUENCE: 32

Cys Ala Ser Ser Gln Gly Leu Leu Leu Asp Asn Glu Gln Phe Phe
1               5                   10                  15

<210> SEQ ID NO 33
<211> LENGTH: 17
<212> TYPE: PRT
<213> ORGANISM: Homo sapiens

<400> SEQUENCE: 33

Cys Ala Ser Ser Ser Pro Met Asp Ser Gly Asp Thr Asp Thr Gln Tyr
1               5                   10                  15

Phe

<210> SEQ ID NO 34
<211> LENGTH: 13
<212> TYPE: PRT
<213> ORGANISM: Homo sapiens

<400> SEQUENCE: 34

Cys Ala Ser Ser Pro Arg Ser Gly Val Pro Gln His Phe
1               5                   10

<210> SEQ ID NO 35
<211> LENGTH: 17
<212> TYPE: PRT
<213> ORGANISM: Homo sapiens

<400> SEQUENCE: 35

-continued

Cys Ala Ser Ser Phe Val Arg Glu Glu Gly Ser Thr Asp Thr Gln Tyr
1               5                   10                  15

Phe

<210> SEQ ID NO 36
<211> LENGTH: 13
<212> TYPE: PRT
<213> ORGANISM: Homo sapiens

<400> SEQUENCE: 36

Cys Ser Ala Arg Gly Thr Glu Ser Tyr Glu Gln Tyr Phe
1               5                   10

<210> SEQ ID NO 37
<211> LENGTH: 15
<212> TYPE: PRT
<213> ORGANISM: Homo sapiens

<400> SEQUENCE: 37

Cys Ala Ser Trp Pro Gly Glu Gly Phe Gly Thr Gln Tyr Phe
1               5                   10                  15

<210> SEQ ID NO 38
<211> LENGTH: 13
<212> TYPE: PRT
<213> ORGANISM: Homo sapiens

<400> SEQUENCE: 38

Cys Ser Gly Trp Gly Gln Gly Asp Glu Lys Leu Phe Phe
1               5                   10

<210> SEQ ID NO 39
<211> LENGTH: 15
<212> TYPE: PRT
<213> ORGANISM: Homo sapiens

<400> SEQUENCE: 39

Cys Ala Ser Ser Glu Tyr Thr Ser Gly Asn Gln Pro Gln His Phe
1               5                   10                  15

<210> SEQ ID NO 40
<211> LENGTH: 16
<212> TYPE: PRT
<213> ORGANISM: Homo sapiens

<400> SEQUENCE: 40

Cys Ser Ala Arg Asp Leu Trp Thr Gly Glu Thr Tyr Glu Gln Tyr Phe
1               5                   10                  15

<210> SEQ ID NO 41
<211> LENGTH: 14
<212> TYPE: PRT
<213> ORGANISM: Homo sapiens

<400> SEQUENCE: 41

Cys Ser Ala Thr Gly Leu Ala Gly Leu Gly Glu Gln Phe Phe
1               5                   10

<210> SEQ ID NO 42
<211> LENGTH: 15
<212> TYPE: PRT
<213> ORGANISM: Homo sapiens

<400> SEQUENCE: 42

```
Cys Ala Thr Ser Asp Leu Gly Thr Gly Val Gly Glu Gln Phe Phe
1               5                   10                  15
```

<210> SEQ ID NO 43
<211> LENGTH: 13
<212> TYPE: PRT
<213> ORGANISM: Homo sapiens

<400> SEQUENCE: 43

```
Cys Ser Val Gly Pro Gly Ser Thr Gly Glu Leu Phe Phe
1               5                   10
```

<210> SEQ ID NO 44
<211> LENGTH: 12
<212> TYPE: PRT
<213> ORGANISM: Homo sapiens

<400> SEQUENCE: 44

```
Cys Ala Ser Ser Pro Thr Gly Glu Lys Leu Phe Phe
1               5                   10
```

<210> SEQ ID NO 45
<211> LENGTH: 16
<212> TYPE: PRT
<213> ORGANISM: Homo sapiens

<400> SEQUENCE: 45

```
Cys Ala Ser Ser Gln Glu Gly Gly Thr Trp Gly Asp Gly Tyr Thr Phe
1               5                   10                  15
```

<210> SEQ ID NO 46
<211> LENGTH: 20
<212> TYPE: PRT
<213> ORGANISM: Homo sapiens

<400> SEQUENCE: 46

```
Cys Ala Thr Ser Asp Leu Leu Leu Ala Gly Gly Arg Ser Ser Tyr Asn
1               5                   10                  15

Glu Gln Phe Phe
            20
```

<210> SEQ ID NO 47
<211> LENGTH: 14
<212> TYPE: PRT
<213> ORGANISM: Homo sapiens

<400> SEQUENCE: 47

```
Cys Ala Ser Ser Glu Ala Ala Ser Gly Arg Pro Gln Thr Phe
1               5                   10
```

<210> SEQ ID NO 48
<211> LENGTH: 19
<212> TYPE: PRT
<213> ORGANISM: Homo sapiens

<400> SEQUENCE: 48

```
Cys Ala Thr Ser Asp Ala Thr Ala Gly Thr Ser Gly Ser Leu Tyr Glu
1               5                   10                  15

Gln Tyr Phe
```

<210> SEQ ID NO 49
<211> LENGTH: 14
<212> TYPE: PRT

<400> SEQUENCE: 49

Cys Ala Ser Ser Leu Thr Gly Leu Gly Gln Pro Gln His Phe
1               5                   10

<210> SEQ ID NO 50
<211> LENGTH: 14
<212> TYPE: PRT
<213> ORGANISM: Homo sapiens

<400> SEQUENCE: 50

Cys Ala Ser Ser Pro Ala Val Leu Ser Tyr Glu Gln Tyr Phe
1               5                   10

<210> SEQ ID NO 51
<211> LENGTH: 15
<212> TYPE: PRT
<213> ORGANISM: Homo sapiens

<400> SEQUENCE: 51

Cys Ser Ala Arg Glu Ser Leu Ala Glu Thr Tyr Glu Gln Tyr Phe
1               5                   10                  15

<210> SEQ ID NO 52
<211> LENGTH: 14
<212> TYPE: PRT
<213> ORGANISM: Homo sapiens

<400> SEQUENCE: 52

Cys Ala Ser Ser Pro Gly Leu Thr Ala Asn Val Leu Thr Phe
1               5                   10

<210> SEQ ID NO 53
<211> LENGTH: 14
<212> TYPE: PRT
<213> ORGANISM: Homo sapiens

<400> SEQUENCE: 53

Cys Ala Ser Ser Leu Gly Leu Ala Gly Asn Glu Gln Tyr Phe
1               5                   10

<210> SEQ ID NO 54
<211> LENGTH: 14
<212> TYPE: PRT
<213> ORGANISM: Homo sapiens

<400> SEQUENCE: 54

Cys Ala Ser Ser Asn Gly Phe His Phe Asn Thr Gln Tyr Phe
1               5                   10

<210> SEQ ID NO 55
<211> LENGTH: 14
<212> TYPE: PRT
<213> ORGANISM: Homo sapiens

<400> SEQUENCE: 55

Cys Ala Ser Ser Leu Gly Ile Leu Thr Asp Thr Gln Tyr Phe
1               5                   10

<210> SEQ ID NO 56
<211> LENGTH: 13
<212> TYPE: PRT
<213> ORGANISM: Homo sapiens

<400> SEQUENCE: 56

Cys Ala Ser Ser Phe Gln Pro Val Asp Thr Gln Tyr Phe
1               5                   10

<210> SEQ ID NO 57
<211> LENGTH: 13
<212> TYPE: PRT
<213> ORGANISM: Homo sapiens

<400> SEQUENCE: 57

Cys Ser Ala Ser Glu Gly Ile Gly Gln Pro Gln His Phe
1               5                   10

<210> SEQ ID NO 58
<211> LENGTH: 12
<212> TYPE: PRT
<213> ORGANISM: Homo sapiens

<400> SEQUENCE: 58

Cys Ala Ser Ser Val Ser Gly Gly Glu Gln Phe Phe
1               5                   10

<210> SEQ ID NO 59
<211> LENGTH: 17
<212> TYPE: PRT
<213> ORGANISM: Homo sapiens

<400> SEQUENCE: 59

Cys Ala Thr Ser Asp Arg Gly Gln Gly Ala Asn Trp Asp Glu Gln Phe
1               5                   10                  15
Phe

<210> SEQ ID NO 60
<211> LENGTH: 13
<212> TYPE: PRT
<213> ORGANISM: Homo sapiens

<400> SEQUENCE: 60

Cys Ala Ser Thr Leu Gly Gly Gly Thr Glu Ala Phe Phe
1               5                   10

<210> SEQ ID NO 61
<211> LENGTH: 15
<212> TYPE: PRT
<213> ORGANISM: Homo sapiens

<400> SEQUENCE: 61

Cys Ser Ala Arg Asp Leu Leu Ala Glu Thr Tyr Glu Gln Tyr Phe
1               5                   10                  15

<210> SEQ ID NO 62
<211> LENGTH: 13
<212> TYPE: PRT
<213> ORGANISM: Homo sapiens

<400> SEQUENCE: 62

Cys Ala Ser Ser Ser Ser Asp Thr Asp Thr Gln Tyr Phe
1               5                   10

<210> SEQ ID NO 63
<211> LENGTH: 18
<212> TYPE: PRT
<213> ORGANISM: Homo sapiens

<400> SEQUENCE: 63

```
Cys Ser Val Glu Gly Ser Leu Gly Arg Ala Leu Arg Ala Asn Glu Gln
1               5                   10                  15

Phe Phe

<210> SEQ ID NO 64
<211> LENGTH: 11
<212> TYPE: PRT
<213> ORGANISM: Homo sapiens

<400> SEQUENCE: 64

Cys Ala Thr His Gly Gly Glu Lys Leu Phe Phe
1               5                   10

<210> SEQ ID NO 65
<211> LENGTH: 14
<212> TYPE: PRT
<213> ORGANISM: Homo sapiens

<400> SEQUENCE: 65

Cys Ala Ser Ser Tyr Val Gly Leu Gly Ser Pro Leu His Phe
1               5                   10

<210> SEQ ID NO 66
<211> LENGTH: 11
<212> TYPE: PRT
<213> ORGANISM: Homo sapiens

<400> SEQUENCE: 66

Cys Ser Gly Gln Ala Asn Thr Glu Ala Phe Phe
1               5                   10

<210> SEQ ID NO 67
<211> LENGTH: 17
<212> TYPE: PRT
<213> ORGANISM: Homo sapiens

<400> SEQUENCE: 67

Cys Ala Ser Ser Pro Thr Thr Gly Leu Lys Thr Arg Ser Gly Tyr Thr
1               5                   10                  15

Phe

<210> SEQ ID NO 68
<211> LENGTH: 12
<212> TYPE: PRT
<213> ORGANISM: Homo sapiens

<400> SEQUENCE: 68

Cys Ser Glu Gly Ser Pro Tyr Asn Glu Gln Phe Phe
1               5                   10

<210> SEQ ID NO 69
<211> LENGTH: 14
<212> TYPE: PRT
<213> ORGANISM: Homo sapiens

<400> SEQUENCE: 69

Cys Ala Ser Ser Asn Gly Phe His Phe Asn Thr Leu Tyr Phe
1               5                   10

<210> SEQ ID NO 70
<211> LENGTH: 13
<212> TYPE: PRT
<213> ORGANISM: Homo sapiens
```

-continued

<400> SEQUENCE: 70

Cys Ala Ser Ser Leu Gly Gly Gly Asp Thr Gln Tyr Phe
1               5                   10

<210> SEQ ID NO 71
<211> LENGTH: 10
<212> TYPE: PRT
<213> ORGANISM: Homo sapiens

<400> SEQUENCE: 71

Glu Ala Ala Gly Ile Gly Ile Leu Thr Val
1               5                   10

<210> SEQ ID NO 72
<211> LENGTH: 10
<212> TYPE: PRT
<213> ORGANISM: Homo sapiens

<400> SEQUENCE: 72

Leu Leu Leu Gly Ile Gly Ile Leu Val Leu
1               5                   10

<210> SEQ ID NO 73
<211> LENGTH: 10
<212> TYPE: PRT
<213> ORGANISM: Homo sapiens

<400> SEQUENCE: 73

Asn Leu Ser Ala Leu Gly Ile Phe Ser Thr
1               5                   10

<210> SEQ ID NO 74
<211> LENGTH: 9
<212> TYPE: PRT
<213> ORGANISM: Homo sapiens

<400> SEQUENCE: 74

Arg Leu Val Asp Asp Phe Leu Leu Val
1               5

<210> SEQ ID NO 75
<211> LENGTH: 9
<212> TYPE: PRT
<213> ORGANISM: Homo sapiens

<400> SEQUENCE: 75

Ala Leu Lys Asp Val Glu Glu Arg Val
1               5

<210> SEQ ID NO 76
<211> LENGTH: 10
<212> TYPE: PRT
<213> ORGANISM: Homo sapiens

<400> SEQUENCE: 76

Ile Thr Ser Ala Ile Gly Val Leu Pro Val
1               5                   10

<210> SEQ ID NO 77
<211> LENGTH: 10
<212> TYPE: PRT
<213> ORGANISM: Homo sapiens

<400> SEQUENCE: 77

Ile Thr Ser Ala Ile Gly Ile Leu Pro Val
1               5                   10

<210> SEQ ID NO 78
<211> LENGTH: 10
<212> TYPE: PRT
<213> ORGANISM: Homo sapiens

<400> SEQUENCE: 78

Met Thr Ser Ala Ile Gly Val Leu Pro Val
1               5                   10

<210> SEQ ID NO 79
<211> LENGTH: 10
<212> TYPE: PRT
<213> ORGANISM: Homo sapiens

<400> SEQUENCE: 79

Gln Thr Ser Ala Ile Gly Val Leu Pro Val
1               5                   10

<210> SEQ ID NO 80
<211> LENGTH: 10
<212> TYPE: PRT
<213> ORGANISM: Homo sapiens

<400> SEQUENCE: 80

Met Thr Ser Ala Ile Gly Ile Leu Pro Val
1               5                   10

<210> SEQ ID NO 81
<211> LENGTH: 10
<212> TYPE: PRT
<213> ORGANISM: Homo sapiens

<400> SEQUENCE: 81

Leu Thr Ser Ala Ile Gly Val Leu Pro Val
1               5                   10

<210> SEQ ID NO 82
<211> LENGTH: 10
<212> TYPE: PRT
<213> ORGANISM: Homo sapiens

<400> SEQUENCE: 82

Ile Thr Ser Gly Ile Gly Val Leu Pro Val
1               5                   10

<210> SEQ ID NO 83
<211> LENGTH: 10
<212> TYPE: PRT
<213> ORGANISM: Homo sapiens

<400> SEQUENCE: 83

Ile Thr Ser Ala Ile Gly Val Leu Pro Ile
1               5                   10

<210> SEQ ID NO 84
<211> LENGTH: 10
<212> TYPE: PRT
<213> ORGANISM: Homo sapiens

<400> SEQUENCE: 84

Gln Thr Ser Ala Ile Gly Ile Leu Pro Val

```
<210> SEQ ID NO 85
<211> LENGTH: 10
<212> TYPE: PRT
<213> ORGANISM: Homo sapiens

<400> SEQUENCE: 85

Ile Thr Ser Ala Ile Gly Val Leu Phe Val
1               5                   10

<210> SEQ ID NO 86
<211> LENGTH: 10
<212> TYPE: PRT
<213> ORGANISM: Homo sapiens

<400> SEQUENCE: 86

Ala Leu Trp Gly Pro Asp Pro Ala Ala Ala
1               5                   10

<210> SEQ ID NO 87
<211> LENGTH: 118
<212> TYPE: PRT
<213> ORGANISM: Homo sapiens

<400> SEQUENCE: 87

Met Pro Arg Glu Asp Ala His Phe Ile Tyr Gly Tyr Pro Lys Lys Gly
1               5                   10                  15

His Gly His Ser Tyr Thr Thr Ala Glu Glu Ala Ala Gly Ile Gly Ile
            20                  25                  30

Leu Thr Val Ile Leu Gly Val Leu Leu Leu Ile Gly Cys Trp Tyr Cys
        35                  40                  45

Arg Arg Arg Asn Gly Tyr Arg Ala Leu Met Asp Lys Ser Leu His Val
    50                  55                  60

Gly Thr Gln Cys Ala Leu Thr Arg Arg Cys Pro Gln Glu Gly Phe Asp
65                  70                  75                  80

His Arg Asp Ser Lys Val Ser Leu Gln Glu Lys Asn Cys Glu Pro Val
                85                  90                  95

Val Pro Asn Ala Pro Pro Ala Tyr Glu Lys Leu Ser Ala Glu Gln Ser
            100                 105                 110

Pro Pro Pro Tyr Ser Pro
        115

<210> SEQ ID NO 88
<211> LENGTH: 24
<212> TYPE: PRT
<213> ORGANISM: Artificial Sequence
<220> FEATURE:
<223> OTHER INFORMATION: Melan A KO

<400> SEQUENCE: 88

Met Pro Arg Glu Asp Ala His Phe Ile Tyr Gly Tyr Pro Lys Lys Gly
1               5                   10                  15

His Gly His Ser Tyr Asn His Gly
            20
```